United States Patent
Mahadevan

(10) Patent No.: US 11,958,824 B2
(45) Date of Patent: *Apr. 16, 2024

(54) PHOTOSTABLE MIMICS OF MACULAR PIGMENT

(71) Applicant: Johnson & Johnson Vision Care, Inc., Jacksonville, FL (US)

(72) Inventor: Shivkumar Mahadevan, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 619 days.

This patent is subject to a terminal disclaimer.

(21) Appl. No.: 16/898,638

(22) Filed: Jun. 11, 2020

(65) Prior Publication Data
US 2020/0407337 A1 Dec. 31, 2020

Related U.S. Application Data

(60) Provisional application No. 62/867,968, filed on Jun. 28, 2019.

(51) Int. Cl.
| | |
|---|---|
| C07D 335/12 | (2006.01) |
| G02B 1/04 | (2006.01) |
| C08K 5/00 | (2006.01) |
| C08L 83/04 | (2006.01) |

(52) U.S. Cl.
CPC .......... *C07D 335/12* (2013.01); *G02B 1/043* (2013.01); *C08K 5/005* (2013.01); *C08L 83/04* (2013.01)

(58) Field of Classification Search
CPC combination set(s) only.
See application file for complete search history.

(56) References Cited

U.S. PATENT DOCUMENTS

| | | |
|---|---|---|
| 3,196,150 A | 7/1965 | Grisar |
| 3,376,303 A | 4/1968 | Fuchs et al. |
| 3,408,429 A | 10/1968 | Wichterle |
| 3,660,545 A | 5/1972 | Wichterle |
| 3,769,294 A | 10/1973 | Catino et al. |
| 3,808,178 A | 4/1974 | Gaylord |

(Continued)

FOREIGN PATENT DOCUMENTS

| | | | |
|---|---|---|---|
| CN | 106349212 A | 1/2017 | |
| CN | 108586289 A * | 9/2018 | ........... C07C 255/34 |

(Continued)

OTHER PUBLICATIONS

Beatty et al., "Macular pigment and age related macular degeneration," Br. J. Ophthalmol. 1999, vol. 83, pp. 867-877.

(Continued)

*Primary Examiner* — Peter A Salamon
(74) *Attorney, Agent, or Firm* — Raef M. Shaltout

(57) ABSTRACT

Described are visible light absorbing compounds. The compounds have a visible light absorption maximum between 430 and 480 nm and a full width half maximum (FWHM) at the visible light absorption maximum of at least 35 nm and up to 100 nanometers, wherein the compounds are photostable. The compounds substantially mimic the visible light absorbance properties of macular pigment while remaining photostable. The compounds may be used in a variety of articles, including ophthalmic devices.

13 Claims, 3 Drawing Sheets

(56) References Cited

U.S. PATENT DOCUMENTS

| | | | |
|---|---|---|---|
| 4,113,224 A | 9/1978 | Clark et al. | |
| 4,120,570 A | 10/1978 | Gaylord | |
| 4,136,250 A | 1/1979 | Mueller et al. | |
| 4,153,641 A | 5/1979 | Deichert et al. | |
| 4,197,266 A | 4/1980 | Clark et al. | |
| 4,436,887 A | 3/1984 | Chromecek et al. | |
| 4,495,313 A | 1/1985 | Larsen | |
| 4,659,782 A | 4/1987 | Spinelli | |
| 4,659,783 A | 4/1987 | Spinelli | |
| 4,740,533 A | 4/1988 | Su et al. | |
| 4,889,664 A | 12/1989 | Kindt-Larsen et al. | |
| 4,910,277 A | 3/1990 | Bambury et al. | |
| 5,006,622 A | 4/1991 | Kunzler et al. | |
| 5,034,461 A | 7/1991 | Lai et al. | |
| 5,039,459 A | 8/1991 | Kindt-Larsen et al. | |
| 5,070,215 A | 12/1991 | Bambury et al. | |
| 5,236,969 A | 8/1993 | Kunzler et al. | |
| 5,244,981 A | 9/1993 | Seidner et al. | |
| 5,270,418 A | 12/1993 | Kunzler et al. | |
| 5,298,533 A | 3/1994 | Nandu et al. | |
| 5,314,960 A | 5/1994 | Spinelli et al. | |
| 5,331,067 A | 7/1994 | Seidner et al. | |
| 5,371,147 A | 12/1994 | Spinelli et al. | |
| 5,470,932 A | 11/1995 | Jinkerson | |
| 5,480,927 A | 1/1996 | Janssen et al. | |
| 5,729,322 A | 3/1998 | Collins et al. | |
| 5,760,100 A | 6/1998 | Nicolson et al. | |
| 5,776,999 A | 7/1998 | Nicolson et al. | |
| 5,789,461 A | 8/1998 | Nicolson et al. | |
| 5,824,719 A | 10/1998 | Kunzler et al. | |
| 5,849,811 A | 12/1998 | Nicolson et al. | |
| 5,872,118 A | 2/1999 | Kelley et al. | |
| 5,916,719 A * | 6/1999 | Kim | C09B 11/28 358/1.15 |
| 5,944,853 A | 8/1999 | Molock et al. | |
| 5,945,465 A | 8/1999 | Ozark et al. | |
| 5,962,548 A | 10/1999 | Vanderlaan et al. | |
| 5,965,631 A | 10/1999 | Nicolson et al. | |
| 5,977,219 A | 11/1999 | Ravichandran et al. | |
| 5,998,498 A | 12/1999 | Vanderlaan et al. | |
| 6,020,445 A | 2/2000 | Vanderlaan et al. | |
| 6,087,415 A | 7/2000 | Vanderlaan et al. | |
| 6,158,862 A | 12/2000 | Patel et al. | |
| 6,166,218 A | 12/2000 | Ravichandran et al. | |
| 6,244,707 B1 | 6/2001 | Faubl | |
| 6,367,929 B1 | 4/2002 | Maiden et al. | |
| 6,373,615 B1 | 4/2002 | Mann et al. | |
| 6,420,453 B1 | 7/2002 | Bowers et al. | |
| 6,423,761 B1 | 7/2002 | Bowers et al. | |
| 6,767,979 B1 | 7/2004 | Muir et al. | |
| 6,822,016 B2 | 11/2004 | McCabe et al. | |
| 6,867,245 B2 | 3/2005 | Iwata et al. | |
| 6,918,931 B2 | 7/2005 | Lai et al. | |
| 6,943,203 B2 | 9/2005 | Vanderlaan et al. | |
| 6,951,894 B1 | 10/2005 | Nicolson et al. | |
| 7,033,391 B2 | 4/2006 | Lai et al. | |
| 7,052,131 B2 | 5/2006 | McCabe et al. | |
| 7,247,692 B2 | 7/2007 | Laredo | |
| 7,249,848 B2 | 7/2007 | Laredo et al. | |
| 7,276,544 B2 | 10/2007 | Lai et al. | |
| 7,396,890 B2 | 7/2008 | Zanini et al. | |
| 7,461,937 B2 | 12/2008 | Steffen et al. | |
| 7,468,398 B2 | 12/2008 | Nicolson et al. | |
| 7,538,146 B2 | 5/2009 | Nicolson et al. | |
| 7,553,880 B2 | 6/2009 | Nicolson et al. | |
| 7,572,841 B2 | 8/2009 | Chen et al. | |
| 7,666,921 B2 | 2/2010 | McCabe et al. | |
| 7,691,916 B2 | 4/2010 | McCabe et al. | |
| 7,691,918 B2 | 4/2010 | Jinkerson et al. | |
| 7,728,051 B2 | 6/2010 | Weinschenk, III et al. | |
| 7,781,571 B2 | 8/2010 | Weinschenk, III et al. | |
| 7,786,185 B2 | 8/2010 | Rathore et al. | |
| 7,803,359 B1 | 9/2010 | Jinkerson et al. | |
| 7,825,170 B2 | 11/2010 | Steffen et al. | |
| 7,915,323 B2 | 3/2011 | Awasthi et al. | |
| 7,934,830 B2 | 5/2011 | Blackwell et al. | |
| 7,956,131 B2 | 6/2011 | Arnold et al. | |
| 7,994,356 B2 | 8/2011 | Awasthi et al. | |
| 8,022,158 B2 | 9/2011 | Rathore et al. | |
| 8,026,326 B2 | 9/2011 | Benz et al. | |
| 8,043,607 B2 | 10/2011 | Jinkerson | |
| 8,138,290 B2 | 3/2012 | Blackwell et al. | |
| 8,153,703 B2 | 4/2012 | Laredo | |
| 8,163,206 B2 | 4/2012 | Chang et al. | |
| 8,207,244 B2 | 6/2012 | Laredo | |
| 8,236,053 B1 | 8/2012 | Freeman | |
| 8,262,947 B2 | 9/2012 | Laredo | |
| 8,262,948 B2 | 9/2012 | Laredo et al. | |
| 8,273,802 B2 | 9/2012 | Laredo et al. | |
| 8,323,631 B2 | 12/2012 | Jinkerson | |
| 8,329,775 B2 | 12/2012 | Laredo | |
| 8,360,574 B2 | 1/2013 | Ishak et al. | |
| 8,389,597 B2 | 3/2013 | Blackwell et al. | |
| 8,399,538 B2 | 3/2013 | Steffen | |
| 8,415,404 B2 | 4/2013 | Nicolson et al. | |
| 8,420,711 B2 | 4/2013 | Awasthi et al. | |
| 8,450,387 B2 | 5/2013 | McCabe et al. | |
| 8,470,906 B2 | 6/2013 | Rathore et al. | |
| 8,476,390 B2 | 7/2013 | Benz et al. | |
| 8,487,058 B2 | 7/2013 | Liu et al. | |
| 8,507,577 B2 | 8/2013 | Zanini et al. | |
| 8,568,626 B2 | 10/2013 | Nicolson et al. | |
| 8,585,938 B1 | 11/2013 | Jinkerson et al. | |
| 8,618,323 B2 | 12/2013 | Benz et al. | |
| 8,637,621 B2 | 1/2014 | Iwata et al. | |
| 8,703,891 B2 | 4/2014 | Broad | |
| 8,784,867 B2 | 7/2014 | Samuel et al. | |
| 8,807,745 B2 | 8/2014 | Nunez et al. | |
| 8,940,812 B2 | 1/2015 | Reboul et al. | |
| 8,980,972 B2 | 3/2015 | Driver | |
| 9,005,700 B2 | 4/2015 | Bothe et al. | |
| 9,056,878 B2 | 6/2015 | Fujisawa et al. | |
| 9,057,821 B2 | 6/2015 | Broad et al. | |
| 9,125,829 B2 | 9/2015 | Bonda et al. | |
| 9,145,383 B2 | 9/2015 | Bonda et al. | |
| 9,170,349 B2 | 10/2015 | Mahadevan et al. | |
| 9,217,813 B2 | 12/2015 | Liu et al. | |
| 9,244,196 B2 | 1/2016 | Scales et al. | |
| 9,249,249 B2 | 2/2016 | Awasthi et al. | |
| 9,260,544 B2 | 2/2016 | Rathore et al. | |
| 9,278,949 B2 | 3/2016 | Loccufier | |
| 9,297,928 B2 | 3/2016 | Molock et al. | |
| 9,297,929 B2 | 3/2016 | Scales et al. | |
| 9,315,669 B2 | 4/2016 | Holland et al. | |
| 9,611,246 B2 | 4/2017 | Bonda et al. | |
| 9,637,444 B2 | 5/2017 | Qian | |
| 9,765,051 B2 | 9/2017 | Bonda et al. | |
| 9,867,800 B2 | 1/2018 | Bonda et al. | |
| 9,926,289 B2 | 3/2018 | Bonda et al. | |
| 9,927,635 B2 | 3/2018 | Ishak et al. | |
| 9,957,258 B2 | 5/2018 | Kunimoto et al. | |
| 10,113,075 B2 | 10/2018 | Nesvadba et al. | |
| 10,268,053 B2 | 4/2019 | Holland et al. | |
| 10,338,408 B2 | 7/2019 | Bothe et al. | |
| 10,597,515 B2 | 3/2020 | Nesvadba et al. | |
| 10,935,695 B2 | 3/2021 | Mahadevan et al. | |
| 11,401,400 B2 | 8/2022 | Shishino et al. | |
| 11,543,683 B2 | 1/2023 | Mahadevan et al. | |
| 2002/0042653 A1 | 4/2002 | Copeland et al. | |
| 2004/0070726 A1 | 4/2004 | Ishak | |
| 2005/0018131 A1 | 1/2005 | Ishak | |
| 2005/0055090 A1 | 3/2005 | Lai et al. | |
| 2005/0055091 A1 | 3/2005 | Lai et al. | |
| 2005/0243272 A1 | 11/2005 | Mainster et al. | |
| 2005/0254003 A1 | 11/2005 | Jani et al. | |
| 2006/0092374 A1 | 5/2006 | Ishak | |
| 2006/0252850 A1 | 11/2006 | Jani et al. | |
| 2007/0092830 A1 | 4/2007 | Lai et al. | |
| 2007/0092831 A1 | 4/2007 | Lai et al. | |
| 2007/0100018 A1 | 5/2007 | Hagting et al. | |
| 2007/0216861 A1 | 9/2007 | Ishak et al. | |
| 2008/0002147 A1 | 1/2008 | Haywood et al. | |
| 2010/0048847 A1 | 2/2010 | Broad | |
| 2010/0113641 A1 | 5/2010 | Laredo | |

(56) References Cited

U.S. PATENT DOCUMENTS

| | | |
|---|---|---|
| 2010/0168359 A1 | 7/2010 | Domschke et al. |
| 2010/0321632 A1 | 12/2010 | Sanger |
| 2011/0245818 A1 | 10/2011 | Weinschenk, III |
| 2011/0249234 A1 | 10/2011 | Duis et al. |
| 2012/0196951 A1 | 8/2012 | Mentak |
| 2012/0262792 A1 | 10/2012 | Goldberg et al. |
| 2013/0009059 A1 | 1/2013 | Caruso |
| 2013/0095235 A1 | 4/2013 | Bothe et al. |
| 2013/0168617 A1 | 7/2013 | Alli et al. |
| 2013/0172440 A1 | 7/2013 | Alii et al. |
| 2013/0217620 A1 | 8/2013 | Alli et al. |
| 2014/0024791 A1 | 1/2014 | Alii et al. |
| 2014/0031447 A1 | 1/2014 | Alii et al. |
| 2014/0044654 A1 | 2/2014 | Bonda et al. |
| 2014/0050681 A1 | 2/2014 | Bonda et al. |
| 2014/0093661 A1 | 4/2014 | Trajkovska et al. |
| 2014/0178595 A1 | 6/2014 | Bothe et al. |
| 2015/0092155 A1 | 4/2015 | Chang et al. |
| 2015/0094395 A1 | 4/2015 | Alli et al. |
| 2015/0164852 A1* | 6/2015 | Bonda ................ C07C 325/02 424/59 |
| 2015/0175732 A1 | 6/2015 | Awasthi et al. |
| 2015/0316688 A1 | 11/2015 | Cefalo et al. |
| 2016/0002200 A1 | 1/2016 | Bonda et al. |
| 2016/0022555 A1 | 1/2016 | Bonda et al. |
| 2017/0038605 A1 | 2/2017 | Legerton |
| 2017/0075137 A1 | 3/2017 | Lin et al. |
| 2017/0131574 A1 | 5/2017 | Lee |
| 2017/0261768 A1 | 9/2017 | Ambler et al. |
| 2018/0037690 A1 | 2/2018 | Aitken et al. |
| 2018/0164608 A1 | 6/2018 | Schmeder et al. |
| 2018/0208583 A1 | 7/2018 | Kunimoto et al. |
| 2018/0263951 A1 | 9/2018 | Bonda et al. |
| 2019/0002459 A1 | 1/2019 | Mahadevan et al. |
| 2019/0121162 A1 | 4/2019 | Alli et al. |
| 2019/0169438 A1 | 6/2019 | Fromentin et al. |
| 2019/0179170 A1 | 6/2019 | Chang et al. |
| 2019/0271798 A1* | 9/2019 | Mahadevan ......... C07D 311/78 |
| 2020/0347166 A1 | 11/2020 | Alli et al. |
| 2020/0347167 A1 | 11/2020 | Alli et al. |
| 2020/0407324 A1 | 12/2020 | Mahadevan et al. |
| 2021/0061934 A1 | 3/2021 | Martin et al. |
| 2022/0194944 A1 | 6/2022 | Mahadevan |

FOREIGN PATENT DOCUMENTS

| | | |
|---|---|---|
| CN | 108586289 A | 9/2018 |
| EP | 0080539 B1 | 6/1983 |
| EP | 0131468 B1 | 1/1985 |
| EP | 0924203 A1 | 6/1999 |
| EP | 1870735 A1 | 12/2007 |
| EP | 2123638 A1 | 11/2009 |
| EP | 3052534 81 | 8/2016 |
| EP | 3419961 B1 | 9/2020 |
| GB | 217810 | 6/1924 |
| GB | 2319035 A | 5/1998 |
| JP | H0743918 A | 2/1995 |
| JP | 2004243596 A | 9/2004 |
| JP | 2004277581 | 10/2004 |
| JP | 200850463 A | 3/2008 |
| JP | 4627009 B2 | 2/2011 |
| JP | 5544017 B2 | 7/2014 |
| RU | 2175321 C2 | 10/2001 |
| RU | 2196557 C2 | 1/2003 |
| RU | 2197907 C2 | 2/2003 |
| RU | 2294132 C2 | 10/2006 |
| RU | 2466173 C1 | 11/2012 |
| RU | 2540655 C2 | 9/2014 |
| RU | 2557993 C1 | 7/2015 |
| RU | 2577800 C2 | 3/2016 |
| WO | 1999063366 A1 | 12/1999 |
| WO | 2001030866 A1 | 5/2001 |
| WO | 200212205 A1 | 2/2002 |
| WO | 200242281 A1 | 5/2002 |
| WO | 2003022321 A2 | 3/2003 |
| WO | 2003089519 A1 | 10/2003 |
| WO | 2007050395 A2 | 5/2007 |
| WO | 2008061992 A2 | 5/2008 |
| WO | 2011130139 A1 | 10/2011 |
| WO | 2013055746 A1 | 4/2013 |
| WO | 2014018208 A1 | 1/2014 |
| WO | 2014025370 A1 | 2/2014 |
| WO | 2015048035 A1 | 4/2015 |
| WO | 2016100457 A1 | 3/2016 |
| WO | 2016175619 A1 | 11/2016 |
| WO | 2017/073467 A1 | 5/2017 |
| WO | 2019166971 A1 | 9/2019 |
| WO | WO-2019166971 A1 * | 9/2019 ............... A61F 2/16 |
| WO | 2020261021 A1 | 12/2020 |
| WO | 2020261091 A1 | 12/2020 |

OTHER PUBLICATIONS

Belusa, J. et al, 2-(2-Hydroxyphenyl)benzotriazoles. I. Synthesis and their ultraviolet and infrared spectra, Chem.zvesti 1974, vol. 28, No. 5, pp. 673-679.

Bernstein et al., "Lutein, zeaxanthin, and meso-zeaxanthin: The basic and clinical science underlying carotenoid-based nutritional interventions against ocular disease," Progress in Retinal and Eye Research, vol. 50, pp. 34-66, (2016).

Berthon, et al., Synthesis, Electrochemical and Spectroscopic Properties of Pendant Hydroquinone-and Quinone-Substitued Polypyridyl Ruthenium (11) Complex, Inorganica Chimica Acta, 1993, pp. 3-7, vol. 204.

Boon et al., "Factors Influencing the Chemical Stability of Carotenoids in Foods," Critical Reviews in Food Science and Nutrition, vol. 50, pp. 515-532 (2010).

Burton et al., "B-Carotene autoxidation: oxygen copolymerization, non-vitamin A products, and immunological activity," Can. J. Chem., vol. 92, pp. 305-316 (2014).

Compendium of Polymer Terminology and Nomenclature: IUPAC Recommendations 2008, edited by: Richard G. Jones, Jaroslav Kahovec, Robert Stepto, Edward S. Wilks, Michael Hess, Tatsuki Kitayama, and W. Val Metanomski.

Crivello, Photoinitiators for Free Radical Cationic & Anionic Photopolymerisation, 2nd Edition, vol. III, pp. 275-298, John Wiley and Sons, New York, 1998.

Doutch et al, Ultraviolet Light Transmission through the Human Corneal Stroma Is Reduced in the Periphery, Biophysical Journal, vol. 102, Mar. 2012, pp. 1258-1264.

Hafez et al, Carbonyl and Thiocarbonyl Compounds. V. Synthesis of Newer Unsaturated Nitriles, Carboxylic Acids, and Esters Derived from Xanthene and Thiaxanthene, Journal of Organic Chemistry, vol. 26, pp. 3988-3991, Oct. 1961.

Ham et al., "Retinal sensitivity to damage from short wavelength light." Nature 260 (1976), pp. 153-155.

International Conference on Harmonisation (ICH) of Technical Requirements for Registration of Pharmaceuticals for Human Use guideline, Q1B Photostability Testing of New Drug Substances and Products, published on Nov. 1996.

Jockusch et al, Photostabilization of Endogenous Porphyrins: Excited State Quenching by Fused Ring Cyanoacrylates, Photchemical & Photobiological Sciences, 2014, vol. 13, No. 8, pp. 1180-1184.

Johnston et al., "Biologically Active Polymers from Spontaneous Carotenoid Oxidation: A New Frontier in Carotenoid Activity," Plos One, vol. 9, Issue 10, pp. 1-10 (Oct. 2014).

Larn, et al., Synthesis of Dinucleating Phenanthroline-Based Ligands, Tetrahedron, Jul. 9, 1999, pp. 8377-8384, vol. 55 Issue 28.

Latif et al, Cleavage of Xanthene Ethers A New Route to 9-Substituted Xanthenes, Canadian Journal of Chemistry, vol. 42 (1964), pp. 1736-1740.

Luning, et al., Bimacrocylic 1, 10-Phenanthroline Cyclophanes, Chemische Beri, 1990, pp. 643-645, vol. 123 Issue 3.

PCT International Search Report, dated May 24, 2019, for PCT Int'l Appln. No. PCT/IB2019/051582.

(56) References Cited

OTHER PUBLICATIONS

Reck, et al., Enantiopure Chiral Chiral Concave 1, 10-Phenanthrolines, European Journal of Organic Chemistry, 2016, pp. 1119-1131, vol. 2016 Issue 6.
Ribeiro et al., "Antioxidant and pro-oxidant activities of carotenoids and their oxidation products," Food and Chemical Toxicology, vol. 120, pp. 681-699 (2018).
Statement on Ocular Ultraviolet Radiation Hazards in Sunlight, American Optometric Association, Nov. 10, 1993.
Stringham et al., "Macular Pigment and Visual Performance in Glare: Benefits for Photostress Recovery, Disability Glare, and Visual Discomfort," IOVS, Sep. 2011, vol. 52, No. 10, pp. 7406-7415.
Ty et al., "Oxidation and Thermal Degradation of Carotenoids," Journal of Oil Palm Research, vol. II, No. 1, pp. 62-78 (Jun. 1999).
PCT International Search Report, dated Jul. 23, 2020, for PCT Int'l Appln. No. PCT/IB2020/055485.
Sato, et al ., Synthesis and characterization of electron transporting polymers having thioxanthene derivatives, Synthetic Metals, Jan. 1, 1999, pp. 55-60, vol. 105.
Selvam, et al ., Tunable anchoring groups@acridone-linked triphenylamine based pendant chromophores and their effects on the photovoltaic performance as sensitizers for dye-sensitized solar celist, RSC Advances, Jan. 14, 2016, pp. 109054-109060, vol. 6 Issue 110.
Hammond et al, Contralateral comparison of blue-filtering and non-blue-filtering intraocular lenses: glare disability, heterochromatic contrast, and photostress recovery, Clinical Ophthalmology, 2010, pp. 1465-1473, vol. 4, Dovepress, US.
Chen et al., Dicyanomethylenated Acridone Based Crystals: Torsional Vibration Confinement Induced Emission with Supramolecular Structure Dependent and Stimuli Responsive Characteristics, The Journal of Physical Chemistry, 2016, 587-597, 120.
PCT International Preliminary Report on Patentability, dated Dec. 28, 2021, for PCT Int'l Appln. No. PCT/IB2020/055485.
PCT International Preliminary Report on Patentability, dated Dec. 28, 2021, for PCT Int'l Appln. No. PCT/IB2020/055868.
Takeda et al, Anisotropic Dissociation of π-π Stacking and Flipping-Motion- Induced Crystal Jumping in Alkylacridones and Their Dicyanomethylene Derivatives, Chem. Eur. J., 2016, 7763-7770, 22.
PCT International Preliminary Report on Patentability, dated Mar. 1, 2022, for PCT Int'l Appln. No. PCT/IB2020/057732.
PCT International Preliminary Report on Patentability, dated Mar. 1, 2022, for PCT Int'l Appln. No. PCT/IB2020/057733.
PCT International Search Report, dated Mar. 1, 2022, for PCT Int'l Appln. No. PCT/IB2021/061175.
Bondyreva E. Y., "Polimerization", Methodological Guidelines for Independent Work. Nizhnekamsk Chemical and Technological Institute of the Federal State Budget Educational Institution of Higher Professional Education "Kazan National Research Technological University", Nizhnekamsk, 2014, pp. 4-13.
Kolpashchikova et al., "Organic Chemistry" Part II. Arenes. Halogened Hydrocarbons. Ministry of Education of the Russian Federation. Yaroslavl State Technical University, 1999, p. 14.
Sutjagin et al, "Chemistry and Physics of Polymers," Training Manual. TPU Publishing House, Tomsk, 2003, Chapter 1, p. 9, Chapter 2, pp. 19-56.
Nishino, et al ., Manganese (111)-Mediated Carbon-Carbon Bond Formation in The Reaction Of Xanthenes With Active Methylene Compounds, The journal of organic chemistry, Jan. 1, 1992, pp. 3551-3557, vol. 57.
PCT International Search Report, dated Oct. 9, 2020, for PCT Int'l Appln. No. PCT/IB2020/057732.
PCT International Search Report, dated Oct. 9, 2020, for PCT Int'l Appln. No. PCT/IB2020/057733.
PCT International Search Report, dated Sep. 23, 2020, for PCT Int'l Appln. No. PCT/IB2020/055868.
PCT International Preliminary Report on Patentability, dated Sep. 8, 2020, for PCT Int'l Appln. No. PCT/IB2019/051582.
Chakrabarti et al., "Statistics of Real-World Hyperspectral Images", CVPR 2011, pp. 193-200, Jun. 20-25, 2011.
Das et al., "In vitro and schematic model eye assessment of glare or positive dysphotopsia-type photic phenomena: comparison of a new material IOL to other monofocal IOLs", Journal of Cataract & Refractive Surgery, vol. 45, Issue 2, pp. 219-227, Feb. 2019.
Elsherif et al., "Contact Lenses for Color Vision Deficiency", Advanced Materials Technologies, vol. 6, Issue 1, pp. 1-9, Jan. 2021.
Foster et al., "Frequency of Metamerism in Natural Scenes", Journal of the Optical Society of America A, vol. 23, No. 10, pp. 2359-2372, Oct. 2006.
Harris et al., "Effect of Tinted Contact Lenses on Color Vision", Am J Optom Physiol Opt., vol. 53, No. 3, pp. 145-148, Mar. 1976.
Laxer, "Soft Tinted Contact Lenses and Color Discrimination", International Contact Lens Clinic, vol. 17, pp. 88-91, Mar.-Apr. 1990.
Macleod et al., "Chromaticity Diagram Showing Cone Excitation by Stimuli of Equal Luminance", Journal of the Optical Society of America, vol. 69, Issue 8, pp. 1183-1186, Aug. 1979.
Mencucci et al., "Visual Outcome, Optical Quality and Patients' Satisfaction with a New Monofocal Intraocular Lens, Enhanced for Intermediate Vision: Preliminary Results", Journal of Cataract & Refractive Surgery, vol. 46, Issue 3, pp. 378-387, Mar. 2020.
Miao et al., "Objective Optical Quality and Intraocular Scattering in Myopic Adults", Investigative Ophthalmology & Visual Science, vol. 55, No. 9, pp. 5582-5587, Sep. 2014.
Mostafa et al., "The Effect of Age and Gender on Tear Film Breakup Time", In Egyptian Journal of Medical Research, vol. 2, Issue 2, 11 pages, 2021.
Nascimento et al., "Statistics of Spatial Cone-excitation Ratios in Natural Scenes", Journal of the Optical Society of America A, vol. 19, Issue 8, pp. 1484-1490, Aug. 2002.
Parraga et al., "Color and Luminance Information in Natural Scenes", Journal of the Optical Society of America A, vol. 15, No. 3, pp. 563-569, Mar. 1998.
Patel, et al., "Effect of Visual Display Unit Use on Blink Rate and Tear Stability", In Optom Visual Sci, vol. 68, Issue 11, pp. 888-892, Nov. 1991.
Pokorny et al., "Aging of the Human Lens", Applied Optics, vol. 26, No. 8, pp. 1437-1440, Apr. 1987.
Stockman et al., "The Spectral Sensitivities of the Middle- and Long-wavelength-sensitive Cones Derived from Measurements in Observers of Known Genotype", Vision Research, vol. 40, pp. 1711-1737, 2000.
Tan, et al., "Dynamic Change of Optical Quality in Patients with Dry Eye Disease", In Invest Ophthalmol Vis Sci. vol. 56, Issue 5, pp. 2848-2854, May 2015.
Tester, et al., "Dysphotopsia in phakic and pseudophakic patients: incidence and relation to intraocular lens type", In Journal of Cataract & Refractive Surgery, vol. 26, Issue 6 , pp. 810-816, Jun. 2000.
Tsubota, et al., "Dry Eyes and Video Display Terminals", In New England Journal of Medicine, vol. 328, Issue 8, p. 584, Feb. 25, 1993.
Van den Berg, T. J. T. P, "Importance of Pathological Intraocular Light Scatter for Visual Disability", In Documenta Ophthalmologica, vol. 61, pp. 327-333, 1986.
Xi et al., "Assessment of Tear Film Optical Quality in a Young Short Tear Break-up Time Dry Eye: Case-control study", Medicine, vol. 98, Issue 40, pp. 1-6, 2019.

\* cited by examiner

PHOTOSTABLE MIMICS OF MACULAR PIGMENT

RELATED APPLICATIONS

This application claims priority to U.S. Provisional Patent Application Ser. No. 62/867,968, filed Jun. 28, 2019, which is incorporated herein by reference in its entirety.

FIELD OF THE INVENTION

The invention relates to visible light absorbers. More particularly, the invention relates to compounds that substantially mimic the visible light absorbance properties of macular pigment while remaining photostable. The compounds may be used in a variety of articles, including ophthalmic devices.

BACKGROUND OF THE INVENTION

Human ocular tissues contain the dietary cartenoids lutein (L) and zeaxanthin (Z), collectively known as macular pigment (MP). Several reports describe the benefits of MP, for instance as a short-wavelength (blue light) filter and as a powerful antioxidant, have been made. MP is also believed to play a protective role against age related macular degeneration (AMD) (Bernstein, P. S., Li, B., Vachali, P. P., Gorusupudi, A., Shyam, R., Henriksen, B. S., Nolan, J. M. Prog. Retin. Eye Res. 2016, 50, 34-66; Beatty, S., Boulton, M., Koh, H-H., Murray, I, J. Br. J. Ophthalmol 1999, 83, 867-877). Macular pigment has further been found to correlate significantly with photostress recovery times, reduced disability glare contrast thresholds, and reduced visual discomfort (Stringham, J. M., Garcia., P. V., Smith, P. A., McLin, L, N., Foutch, B. K. IOVS, 2011, 52 (10) 7406-7415).

The chemical entities associated with macular pigment are carotenoid derivatives that possess extensive unsaturation and are highly reactive toward olefin isomerization and oxidation upon photoexcitation. The antioxidant protective mechanism that carotenoids provide is essentially sacrificial, where excitation of the pi system results in the reaction of its excited state with triplet oxygen, thereby protecting/limiting the excitation and reactions of other photosensitive compounds in the ocular environment. See e.g., Ribeiro, et al., Food and Chemical Toxicology, Vol. 120, pp. 681-699 (2018); Burton, et al., Can. J. Chem., Vol. 92, pp. 305-316 (2014); Ty, et al., Journal of Oil Palm Research Vol. II No. 1, pp. 62-78 (June 1999); Johnston, et al., Plos One, Vol. 9(10), pp. 1-10 (2014); and Boon, et al., Critical Reviews in Food Science and Nutrition, Vol. 50, pp. 515-532 (2010).

While the incorporation of macular pigment into products for the purpose of offering ocular protection is desirable, the overall lack of stability (thermal, oxidative, and photochemical) of carotenoids creates a very high barrier to the development of such products. Thus, it would be a significant advance if new stable materials that mimic the light absorbing properties of macular pigment were developed.

SUMMARY OF THE INVENTION

The invention relates to compounds that exhibit visible light absorbance spectra in the 400 to 500 nm wavelength range that substantially mimic the spectrum of macular pigment. Such compounds are also photostable, for instance when measured for changes/loss of absorption characteristics upon exposure to conditions analogous to those described in ICH Q1B. In addition, compounds may exhibit a high extinction coefficient at desired wavelengths in the 400 to 500 nm and may therefore be used in low concentrations to provide their light absorbing benefits. The compounds described herein may, for instance, be used in ophthalmic devices to, for example, supplement the macular pigment optical density (MPOD) of wearers.

Accordingly, in one aspect the invention provides a compound having a visible light absorption maximum between 430 and 480 nm and a full width half maximum (FWHM) at the visible light absorption maximum of at least 35 nm and up to 100 nanometers, wherein the compound is photostable.

In another aspect, the invention provides a compound having a visible light absorption maximum between 430 and 480 nm and a full width half maximum (FWHM) at the visible light absorption maximum of at least 35 nm and up to 100 nanometers, wherein the compound is more photostable than macular pigment.

In a further aspect, the invention provides a compound comprising a chromophore, the chromophore having a substructure of formula I:

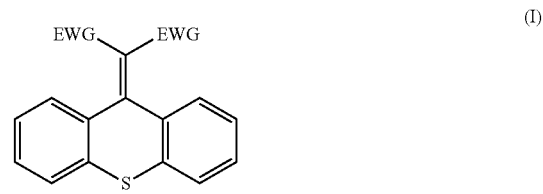

(I)

wherein EWG at each occurrence is independently an electron withdrawing group.

In a still further aspect, the invention provides an ophthalmic device comprising a compound as described herein.

DETAILED DESCRIPTION OF THE INVENTION

Figure 1:
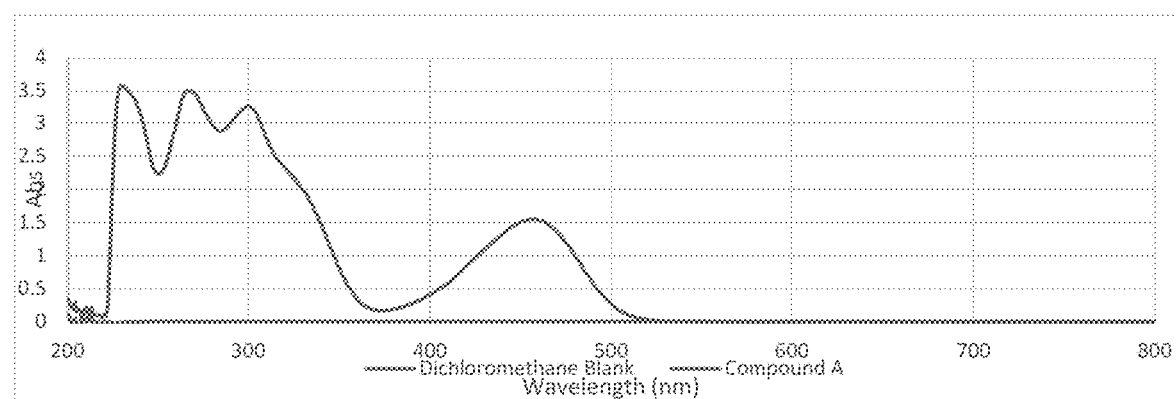
FIG. 1 shows a UV-VIS transmission spectrum of a 0.2 mM methanolic solution of exemplary Compound A of the invention.

It is to be understood that the invention is not limited to the details of construction or process steps set forth in the following description. The invention is capable of other embodiments and of being practiced or being carried out in various ways using the teaching herein.

With respect to the terms used in this disclosure, the following definitions are provided.

Unless defined otherwise, all technical and scientific terms used herein have the same meaning as commonly understood by one of ordinary skill in the art to which the invention belongs. The polymer definitions are consistent with those disclosed in the Compendium of Polymer Terminology and Nomenclature, IUPAC Recommendations 2008, edited by: Richard G. Jones, Jaroslav Kahovec, Robert Stepto, Edward S. Wilks, Michael Hess, Tatsuki Kitayama, and W. Val Metanomski. All publications, patent applications, patents, and other references mentioned herein are incorporated by reference.

As used herein, the term "(meth)" designates optional methyl substitution. Thus, a term such as "(meth)acrylates" denotes both methacrylates and acrylates.

Wherever chemical structures are given, it should be appreciated that alternatives disclosed for the substituents on the structure may be combined in any combination. Thus, if a structure contained substituents R* and R**, each of which contained three lists of potential groups, 9 combinations are disclosed. The same applies for combinations of properties.

When a subscript, such as "n" in the generic formula [***]n, is used to depict the number of repeating units in a polymer's chemical formula, the formula should be interpreted to represent the number average molecular weight of the macromolecule.

The term "individual" includes humans and vertebrates.

The term "biomedical device" refers to any article that is designed to be used while either in or on mammalian tissues or fluids, and preferably in or on human tissue or fluids. Examples of these devices include but are not limited to wound dressings, sealants, tissue fillers, drug delivery systems, coatings, adhesion prevention barriers, catheters, implants, stents, and ophthalmic devices such as intraocular lenses and contact lenses. The biomedical devices may be ophthalmic devices, particularly contact lenses, most particularly contact lenses made from silicone hydrogels or conventional hydrogels.

The term "ocular surface" includes the surface and glandular epithelia of the cornea, conjunctiva, lacrimal gland, accessory lacrimal glands, nasolacrimal duct and meibomian gland, and their apical and basal matrices, puncta and adjacent or related structures, including eyelids linked as a functional system by both continuity of epithelia, by innervation, and the endocrine and immune systems.

The term "ophthalmic device" refers to any optical device relating to the eye and includes devices which resides in or on the eye or any part of the eye, including the ocular surface. These devices can provide optical correction, cosmetic enhancement, vision enhancement, therapeutic benefit (for example as bandages) or delivery of active components such as pharmaceutical and nutraceutical components, or a combination of any of the foregoing. Examples of ophthalmic devices include but are not limited to lenses, optical and ocular inserts, including but not limited to punctal plugs, and the like. "Lenses" include spectacle lenses, sunglass lenses, soft contact lenses, hard contact lenses, hybrid contact lenses, intraocular lenses, and overlay lenses. The ophthalmic device may comprise a contact lens.

The term "contact lens" refers to an ophthalmic device that can be placed on the cornea of an individual's eye. The contact lens may provide corrective, cosmetic, or therapeutic benefit, including wound healing, the delivery of drugs or nutraceuticals, diagnostic evaluation or monitoring, ultraviolet light absorbing, visible light or glare reduction, or any combination thereof. A contact lens can be of any appropriate material known in the art and can be a soft lens, a hard lens, or a hybrid lens containing at least two distinct portions with different physical, mechanical, or optical properties, such as modulus, water content, light transmission, or combinations thereof.

Spectacle lenses or sunglasses may be comprised of mineral material, for example based on silicate, or made from an organic material, such as polycarbonate; polyamide; polyimide; polysulfones; polyethylene terephthalate/polycarbonate copolymers; and various other materials known in the art.

The biomedical devices, ophthalmic devices, and lenses of the present invention may be comprised of silicone hydrogels or conventional hydrogels. Silicone hydrogels typically contain at least one hydrophilic monomer and at least one silicone-containing component that are covalently bound to one another in the cured device.

"Target macromolecule" means the macromolecule being synthesized from the reactive monomer mixture comprising monomers, macromers, prepolymers, cross-linkers, initiators, additives, diluents, and the like.

The term "polymerizable compound" means a compound containing one or more polymerizable groups. The term encompasses, for instance, monomers, macromers, oligomers, prepolymers, cross-linkers, and the like.

"Polymerizable groups" are groups that can undergo chain growth polymerization, such as free radical and/or cationic polymerization, for example a carbon-carbon double bond which can polymerize when subjected to radical polymerization initiation conditions. Non-limiting examples of free radical polymerizable groups include (meth)acrylates, styrenes, vinyl ethers, (meth)acrylamides, N-vinyllactams, N-vinylamides, O-vinylcarbamates, O-vinylcarbonates, and other vinyl groups. Preferably, the free radical polymerizable groups comprise (meth)acrylate, (meth)acrylamide, N-vinyl lactam, N-vinylamide, and styryl functional groups, and mixtures of any of the foregoing. More preferably, the free radical polymerizable groups comprise (meth)acrylates, (meth)acrylamides, and mixtures thereof. The polymerizable group may be unsubstituted or substituted. For instance, the nitrogen atom in (meth)acrylamide may be bonded to a hydrogen, or the hydrogen may be replaced with alkyl or cycloalkyl (which themselves may be further substituted).

Any type of free radical polymerization may be used including but not limited to bulk, solution, suspension, and emulsion as well as any of the controlled radical polymerization methods such as stable free radical polymerization, nitroxide-mediated living polymerization, atom transfer radical polymerization, reversible addition fragmentation chain transfer polymerization, organotellurium mediated living radical polymerization, and the like.

A "monomer" is a mono-functional molecule which can undergo chain growth polymerization, and in particular, free radical polymerization, thereby creating a repeating unit in the chemical structure of the target macromolecule. Some monomers have di-functional impurities that can act as cross-linking agents. A "hydrophilic monomer" is also a monomer which yields a clear single phase solution when mixed with deionized water at 25° C. at a concentration of 5 weight percent. A "hydrophilic component" is a monomer, macromer, prepolymer, initiator, cross-linker, additive, or polymer which yields a clear single phase solution when mixed with deionized water at 25° C. at a concentration of 5 weight percent. A "hydrophobic component" is a monomer, macromer, prepolymer, initiator, cross-linker, additive, or polymer which is slightly soluble or insoluble in deionized water at 25° C.

A "macromolecule" is an organic compound having a number average molecular weight of greater than 1500, and may be reactive or non-reactive.

A "macromonomer" or "macromer" is a macromolecule that has one group that can undergo chain growth polymerization, and in particular, free radical polymerization, thereby creating a repeating unit in the chemical structure of the target macromolecule. Typically, the chemical structure of the macromer is different than the chemical structure of the target macromolecule, that is, the repeating unit of the macromer's pendent group is different than the repeating unit of the target macromolecule or its mainchain. The difference between a monomer and a macromer is merely one of chemical structure, molecular weight, and molecular weight distribution of the pendent group. As a result, and as used herein, the patent literature occasionally defines monomers as polymerizable compounds having relatively low molecular weights of about 1,500 Daltons or less, which inherently includes some macromers. In particular, monomethacryloxypropyl terminated mono-n-butyl terminated polydimethylsiloxane (molecular weight=500-1500 g/mol) (mPDMS) and mono-(2-hydroxy-3-methacryloxy-propyl)-propyl ether terminated mono-n-butyl terminated polydimethylsiloxane (molecular weight=500-1500 g/mol) (OH-mPDMS) may be referred to as monomers or macromers. Furthermore, the patent literature occasionally defines macromers as having one or more polymerizable groups, essentially broadening the common definition of macromer to include prepolymers. As a result and as used herein, di-functional and multi-functional macromers, prepolymers, and crosslinkers may be used interchangeably.

A "silicone-containing component" is a monomer, macromer, prepolymer, cross-linker, initiator, additive, or polymer in the reactive mixture with at least one silicon-oxygen bond, typically in the form of siloxy groups, siloxane groups, carbosiloxane groups, and mixtures thereof.

Examples of silicone-containing components which are useful in this invention may be found in U.S. Pat. Nos. 3,808,178, 4,120,570, 4,136,250, 4,153,641, 4,740,533, 5,034,461, 5,070,215, 5,244,981, 5,314,960, 5,331,067, 5,371,147, 5,760,100, 5,849,811, 5,962,548, 5,965,631, 5,998,498, 6,367,929, 6,822,016, 6,943,203, 6,951,894, 7,052,131, 7,247,692, 7,396,890, 7,461,937, 7,468,398, 7,538,146, 7,553,880, 7,572,841, 7,666,921, 7,691,916, 7,786,185, 7,825,170, 7,915,323, 7,994,356, 8,022,158, 8,163,206, 8,273,802, 8,399,538, 8,415,404, 8,420,711, 8,450,387, 8,487,058, 8,568,626, 8,937,110, 8,937,111, 8,940,812, 8,980,972, 9,056,878, 9,125,808, 9,140,825, 9,156,934, 9,170,349, 9,217,813, 9,244,196, 9,244,197, 9,260,544, 9,297,928, 9,297,929, and European Patent No. 080539. These patents are hereby incorporated by reference in their entireties.

A "polymer" is a target macromolecule composed of the repeating units of the monomers used during polymerization.

A "homopolymer" is a polymer made from one monomer; a "copolymer" is a polymer made from two or more monomers; a "terpolymer" is a polymer made from three monomers. A "block copolymer" is composed of compositionally different blocks or segments. Diblock copolymers have two blocks. Triblock copolymers have three blocks. "Comb or graft copolymers" are made from at least one macromer.

A "repeating unit" is the smallest group of atoms in a polymer that corresponds to the polymerization of a specific monomer or macromer.

An "initiator" is a molecule that can decompose into radicals which can subsequently react with a monomer to initiate a free radical polymerization reaction. A thermal initiator decomposes at a certain rate depending on the temperature; typical examples are azo compounds such as 1,1'-azobisisobutyronitrile and 4,4'-azobis(4-cyanovaleric acid), peroxides such as benzoyl peroxide, tert-butyl peroxide, tert-butyl hydroperoxide, tert-butyl peroxybenzoate, dicumyl peroxide, and lauroyl peroxide, peracids such as peracetic acid and potassium persulfate as well as various redox systems. A photo-initiator decomposes by a photochemical process; typical examples are derivatives of benzil, benzoin, acetophenone, benzophenone, camphorquinone, and mixtures thereof as well as various monoacyl and bisacyl phosphine oxides and combinations thereof.

A "cross-linking agent" is a di-functional or multi-functional monomer or macromer which can undergo free radical polymerization at two or more locations on the molecule, thereby creating branch points and a polymeric network. Common examples are ethylene glycol dimethacrylate, tetraethylene glycol dimethacrylate, trimethylolpropane trimethacrylate, methylene bisacrylamide, triallyl cyanurate, and the like.

A "prepolymer" is a reaction product of monomers which contains remaining polymerizable groups capable of undergoing further reaction to form a polymer.

A "polymeric network" is a cross-linked macromolecule that may swell but cannot dissolve in solvents. "Hydrogels" are polymeric networks that swell in water or aqueous solutions, typically absorbing at least 10 weight percent water. "Silicone hydrogels" are hydrogels that are made from at least one silicone-containing component with at least one hydrophilic component. Hydrophilic components may also include non-reactive polymers.

"Conventional hydrogels" refer to polymeric networks made from components without any siloxy, siloxane or carbosiloxane groups. Conventional hydrogels are prepared from reactive mixtures comprising hydrophilic monomers. Examples include 2-hydroxyethyl methacrylate ("HEMA"), N-vinyl pyrrolidone ("NVP"), N, N-dimethylacrylamide ("DMA") or vinyl acetate. U.S. Pat. Nos. 4,436,887, 4,495,313, 4,889,664, 5,006,622, 5,039459, 5,236,969, 5,270,418, 5,298,533, 5,824,719, 6,420,453, 6,423,761, 6,767,979, 7,934,830, 8,138,290, and 8,389,597 disclose the formation of conventional hydrogels. Commercially available conventional hydrogels include, but are not limited to, etafilcon, genfilcon, hilafilcon, lenefilcon, nesofilcon, omafilcon, polymacon, and vifilcon, including all of their variants.

"Silicone hydrogels" refer to polymeric networks made from at least one hydrophilic component and at least one silicone-containing component. Examples of silicone hydrogels include acquafilcon, asmofilcon, balafilcon, comfilcon, delefilcon, enfilcon, fanfilcon, formofilcon, galyfilcon, lotrafilcon, narafilcon, riofilcon, samfilcon, senofilcon, somofilcon, and stenfilcon, including all of their variants, as well as silicone hydrogels as prepared in U.S. Pat. Nos. 4,659,782, 4,659,783, 5,244,981, 5,314,960, 5,331,067, 5,371,147, 5,998,498, 6,087,415, 5,760,100, 5,776,999, 5,789,461, 5,849,811, 5,965,631, 6,367,929, 6,822,016, 6,867,245, 6,943,203, 7,247,692, 7,249,848, 7,553,880, 7,666,921, 7,786,185, 7,956,131, 8,022,158, 8,273,802, 8,399,538, 8,470,906, 8,450,387, 8,487,058, 8,507,577, 8,637,621, 8,703,891, 8,937,110, 8,937,111, 8,940,812, 9,056,878, 9,057,821, 9,125,808, 9,140,825, 9,156,934, 9,170,349, 9,244,196, 9,244,197, 9,260,544, 9,297,928, 9,297,929 as well as WO 03/22321, WO 2008/061992, and US 2010/0048847. These patents are hereby incorporated by reference in their entireties.

An "interpenetrating polymeric network" comprises two or more networks which are at least partially interlaced on the molecular scale but not covalently bonded to each other and which cannot be separated without braking chemical bonds. A "semi-interpenetrating polymeric network" comprises one or more networks and one or more polymers characterized by some mixing on the molecular level between at least one network and at least one polymer. A mixture of different polymers is a "polymer blend." A semi-interpenetrating network is technically a polymer blend, but in some cases, the polymers are so entangled that they cannot be readily removed.

"Reactive components" are the polymerizable compounds (such as monomers, macromers, oligomers, prepolymers, and cross-linkers) in the reactive mixture (defined below), as well as any other components in the reactive mixture which are intended to substantially remain in the resultant polymeric network after polymerization and all work-up steps (such as extraction steps) and packaging steps have been completed. Reactive components may be retained in the polymeric network by covalent bonding, hydrogen bonding, electrostatic interactions, the formation of interpenetrating polymeric networks, or any other means. Components that are intended to release from the polymeric network once it is in use are still considered "reactive components." For example, pharmaceutical or nutraceutical components in a contact lens which are intended to be released during wear are considered "reactive components." Components that are intended to be removed from the polymeric network during the manufacturing process (e.g., by extraction), such as diluents, are not "reactive components."

The terms "reactive mixture" and "reactive monomer mixture" refer to the mixture of components which are mixed together and, when subjected to polymerization conditions, result in formation of a polymeric network (such as conventional or silicone hydrogels) as well as biomedical devices, ophthalmic devices, and contact lenses made therefrom. The reactive mixture may comprise reactive components such as monomers, macromers, prepolymers, cross-linkers, and initiators, additives such as wetting agents, polymers, dyes, light absorbing compounds such as UV absorbers, pigments, photochromic compounds, pharmaceutical compounds, and/or nutraceutical compounds, any of which may be polymerizable or non-polymerizable but are capable of being retained within the resulting biomedical device (e.g., contact lens). The reactive mixture may also contain other components which are intended to be removed from the device prior to its use, such as diluents. It will be appreciated that a wide range of additives may be added based upon the contact lens which is made and its intended use. Concentrations of components of the reactive mixture are expressed as weight percentages of all reactive components in the reactive mixture, therefore excluding diluents. When diluents are used, their concentrations are expressed as weight percentages based upon the amount of all components in the reactive mixture (including the diluent).

The term "silicone hydrogel contact lens" refers to a hydrogel contact lens that is made from at least one silicone-containing compound. Silicone hydrogel contact lenses generally have increased oxygen permeability compared to conventional hydrogels. Silicone hydrogel contact lenses use both their water and polymer content to transmit oxygen to the eye.

The term "multi-functional" refers to a component having two or more polymerizable groups. The term "mono-functional" refers to a component having one polymerizable group.

The terms "halogen" or "halo" indicate fluorine, chlorine, bromine, and iodine.

"Alkyl" refers to an optionally substituted linear or branched alkyl group containing the indicated number of carbon atoms. If no number is indicated, then alkyl (including any optional substituents on alkyl) may contain 1 to 16 carbon atoms. Preferably, the alkyl group contains 1 to 10 carbon atoms, alternatively 1 to 8 carbon atoms, alternatively 1 to 6 carbon atoms, or alternatively 1 to 4 carbon atoms. Examples of alkyl include methyl, ethyl, propyl, isopropyl, butyl, iso-, sec- and tert-butyl, pentyl, hexyl, heptyl, 3-ethylbutyl, and the like. Examples of substituents on alkyl include 1, 2, or 3 groups independently selected from hydroxy, amino, amido, oxa, carboxy, alkyl carboxy, carbonyl, alkoxy, thioalkyl, carbamate, carbonate, halogen, phenyl, benzyl, and combinations thereof. "Alkylene" means a divalent alkyl group, such as —$CH_2$—, —$CH_2CH_2$—, —$CH_2CH_2CH_2$—, —$CH_2CH(CH_3)CH_2$—, and —$CH_2CH_2CH_2CH_2$—.

"Haloalkyl" refers to an alkyl group as defined above substituted with one or more halogen atoms, where each halogen is independently F, Cl, Br or I. A preferred halogen is F. Preferred haloalkyl groups contain 1-6 carbons, more preferably 1-4 carbons, and still more preferably 1-2 carbons. "Haloalkyl" includes perhaloalkyl groups, such as —$CF_3$— or —$CF_2CF_3$—. "Haloalkylene" means a divalent haloalkyl group, such as —$CH_2CF_2$—.

"Cycloalkyl" refers to an optionally substituted cyclic hydrocarbon containing the indicated number of ring carbon atoms. If no number is indicated, then cycloalkyl may contain 3 to 12 ring carbon atoms. Preferred are $C_3$-$C_8$ cycloalkyl groups, $C_3$-$C_7$ cycloalkyl, more preferably $C_4$-$C_7$ cycloalkyl, and still more preferably $C_5$-$C_6$ cycloalkyl. Examples of cycloalkyl include cyclopropyl, cyclobutyl, cyclopentyl, cyclohexyl, cycloheptyl and cyclooctyl. Examples of substituents on cycloalkyl include 1, 2, or 3 groups independently selected from alkyl, hydroxy, amino, amido, oxa, carbonyl, alkoxy, thioalkyl, amido, carbamate, carbonate, halo, phenyl, benzyl, and combinations thereof. "Cycloalkylene" means a divalent cycloalkyl group, such as 1,2-cyclohexylene, 1,3-cyclohexylene, or 1,4-cyclohexylene.

"Heterocycloalkyl" refers to a cycloalkyl ring or ring system as defined above in which at least one ring carbon has been replaced with a heteroatom selected from nitrogen, oxygen, and sulfur. The heterocycloalkyl ring is optionally fused to or otherwise attached to other heterocycloalkyl rings and/or non-aromatic hydrocarbon rings and/or phenyl rings. Preferred heterocycloalkyl groups have from 5 to 7 members. More preferred heterocycloalkyl groups have 5 or 6 members. Heterocycloalkylene means a divalent heterocycloalkyl group.

"Aryl" refers to an optionally substituted aromatic hydrocarbon ring system containing at least one aromatic ring. The aryl group contains the indicated number of ring carbon atoms. If no number is indicated, then aryl may contain 6 to 14 ring carbon atoms. The aromatic ring may optionally be fused or otherwise attached to other aromatic hydrocarbon rings or non-aromatic hydrocarbon rings. Examples of aryl groups include phenyl, naphthyl, and biphenyl. Preferred examples of aryl groups include phenyl. Examples of substituents on aryl include 1, 2, or 3 groups independently selected from alkyl, hydroxy, amino, amido, oxa, carboxy, alkyl carboxy, carbonyl, alkoxy, thioalkyl, carbamate, carbonate, halo, phenyl, benzyl, and combinations thereof. "Arylene" means a divalent aryl group, for example 1,2-phenylene, 1,3-phenylene, or 1,4-phenylene.

"Heteroaryl" refers to an aryl ring or ring system, as defined above, in which at least one ring carbon atom has been replaced with a heteroatom selected from nitrogen, oxygen, and sulfur. The heteroaryl ring may be fused or otherwise attached to one or more heteroaryl rings, aromatic or nonaromatic hydrocarbon rings or heterocycloalkyl rings. Examples of heteroaryl groups include pyridyl, furyl, and thienyl. "Heteroarylene" means a divalent heteroaryl group.

"Alkoxy" refers to an alkyl group attached to the parent molecular moiety through an oxygen bridge. Examples of alkoxy groups include, for instance, methoxy, ethoxy, propoxy and isopropoxy. "Thioalkyl" means an alkyl group attached to the parent molecule through a sulfur bridge. Examples of thioalkyl groups include, for instance, methylthio, ethylthio, n-propylthio and iso-propylthio. "Aryloxy" refers to an aryl group attached to a parent molecular moiety through an oxygen bridge. Examples include phenoxy. "Cyclic alkoxy" means a cycloalkyl group attached to the parent moiety through an oxygen bridge.

"Alkylamine" refers to an alkyl group attached to the parent molecular moiety through an —NH bridge. Alkyleneamine means a divalent alkylamine group, such as —CH$_2$CH$_2$NH—.

"Siloxanyl" refers to a structure having at least one Si—O—Si bond. Thus, for example, siloxanyl group means a group having at least one Si—O—Si group (i.e. a siloxane group), and siloxanyl compound means a compound having at least one Si—O—Si group. "Siloxanyl" encompasses monomeric (e.g., Si—O—Si) as well as oligomeric/polymeric structures (e.g., —[Si—O]$_n$—, where n is 2 or more). Each silicon atom in the siloxanyl group is substituted with independently selected R$^A$ groups (where R$^A$ is as defined in formula A options (b)-(i)) to complete their valence.

"Silyl" refers to a structure of formula R$_3$Si— and "siloxy" refers to a structure of formula R$_3$Si—O—, where each R in silyl or siloxy is independently selected from trimethylsiloxy, C$_1$-C$_8$ alkyl (preferably C$_1$-C$_3$ alkyl, more preferably ethyl or methyl), and C$_3$—C cycloalkyl.

"Alkyleneoxy" refers to groups of the general formula -(alkylene-O)$_p$— or —(O-alkylene)$_p$-, wherein alkylene is as defined above, and p is from 1 to 200, or from 1 to 100, or from 1 to 50, or from 1 to 25, or from 1 to 20, or from 1 to 10, wherein each alkylene is independently optionally substituted with one or more groups independently selected from hydroxyl, halo (e.g., fluoro), amino, amido, ether, carbonyl, carboxyl, and combinations thereof. If p is greater than 1, then each alkylene may be the same or different and the alkyleneoxy may be in block or random configuration. When alkyleneoxy forms a terminal group in a molecule, the terminal end of the alkyleneoxy may, for instance, be a hydroxy or alkoxy (e.g., HO—[CH$_2$CH$_2$O]$_p$— or CH$_3$O—[CH$_2$CH$_2$O]$_p$—). Examples of alkyleneoxy include polyethyleneoxy, polypropyleneoxy, polybutyleneoxy, and poly (ethyleneoxy-co-propyleneoxy).

"Oxaalkylene" refers to an alkylene group as defined above where one or more non-adjacent CH$_2$ groups have been substituted with an oxygen atom, such as —CH$_2$CH$_2$OCH(CH$_3$)CH$_2$—. "Thiaalkylene" refers to an alkylene group as defined above where one or more non-adjacent CH$_2$ groups have been substituted with a sulfur atom, such as —CH$_2$CH$_2$SCH(CH$_3$)CH$_2$—.

The term "linking group" refers to a moiety that links a polymerizable group to the parent molecule. The linking group may be any moiety that is compatible with the compound of which it is a part, and that does not undesirably interfere with the polymerization of the compound, is stable under the polymerization conditions as well as the conditions for the processing and storage of the final product. For instance, the linking group may be a bond, or it may comprise one or more alkylene, haloalkylene, amide, amine, alkyleneamine, carbamate, ester (—CO$_2$—), arylene, heteroarylene, cycloalkylene, heterocycloalkylene, alkyleneoxy, oxaalkylene, thiaalkylene, haloalkyleneoxy (alkyleneoxy substituted with one or more halo groups, e.g., —OCF$_2$—, —OCF$_2$CF$_2$—, —OCF$_2$CH$_2$—), siloxanyl, alkylenesiloxanyl, or combinations thereof. The linking group may optionally be substituted with 1 or more substituent groups. Suitable substituent groups may include those independently selected from alkyl, halo (e.g., fluoro), hydroxyl, HO-alkyleneoxy, MeO-alkyleneoxy, siloxanyl, siloxy, siloxy-alkyleneoxy-, siloxy-alkylene-alkyleneoxy- (where more than one alkyleneoxy groups may be present and wherein each methylene in alkylene and alkyleneoxy is independently optionally substituted with hydroxyl), ether, amine, carbonyl, carbamate, and combinations thereof. The linking group may also be substituted with a polymerizable group, such as (meth)acrylate (in addition to the polymerizable group to which the linking group is linked).

Preferred linking groups include C$_1$-C$_8$ alkylene (preferably C$_2$-C$_6$ alkylene) and C$_1$-C$_8$ oxaalkylene (preferably C$_2$-C$_6$ oxaalkylene), each of which is optionally substituted with 1 or 2 groups independently selected from hydroxyl and siloxy. Preferred linking groups also include carboxylate, amide, C$_1$-C$_8$ alkylene-carboxylate-C$_1$-C$_8$ alkylene, or C$_1$-C$_8$ alkylene-amide-C$_1$-C$_8$ alkylene.

When the linking group is comprised of combinations of moieties as described above (e.g., alkylene and cycloalkylene), the moieties may be present in any order. For instance, if in Formula A below, L is indicated as being -alkylene-cycloalkylene-, then Rg-L may be either Rg-alkylene-cycloalkylene-, or Rg-cycloalkylene-alkylene-. Notwithstanding this, the listing order represents the preferred order in which the moieties appear in the compound starting from the terminal polymerizable group (Rg or Pg) to which the linking group is attached. For example, if in Formula A, L is indicated as being alkylene-cycloalkylene, then Rg-L is preferably Rg-alkylene-cycloalkylene-.

The term "electron withdrawing group" (EWG) refers to a chemical group which withdraws electron density from the atom or group of atoms to which the electron withdrawing group is attached. Examples of EWGs include, but are not limited to, cyano, amide, ester, keto, or aldehyde. A preferred EWG is cyano (CN).

The terms "light absorbing compound" refers to a chemical material that absorbs light within the visible spectrum (e.g., in the 380 to 780 nm range). A "high energy radiation absorber," "UV/HEV absorber," or "high energy light absorbing compound" is a chemical material that absorbs various wavelengths of ultraviolet light, high energy visible light, or both. A material's ability to absorb certain wavelengths of light can be determined by measuring its UV/Vis transmission or absorbance spectrum.

When the compounds described herein contain olefinic double bonds or other centers of geometric asymmetry, and unless otherwise specified, it is intended that the compounds include the cis, trans, Z- and E-configurations. Likewise, all tautomeric and salt forms are also intended to be included.

The term "optional substituent" means that a hydrogen atom in the underlying moiety is optionally replaced by a substituent. Any substituent may be used that is sterically practical at the substitution site and is synthetically feasible. Identification of a suitable optional substituent is well within the capabilities of an ordinarily skilled artisan. Examples of an "optional substituent" include, without limitation, C$_1$-C$_6$ alkyl, C$_1$-C$_6$ alkoxy, C$_1$-C$_6$ thioalkyl, C$_3$-C$_7$ cycloalkyl, aryl, halo, hydroxy, amino, NR$^4$R$^5$, benzyl, SO$_3$H, SO$_3$Na, or —Y—P$_g$, wherein R$^4$ and R$^5$ are independently H or C$_1$-C$_6$ alkyl, Y is a linking group; and P$_g$ is a polymerizable group. The foregoing substituents may be optionally substituted by an optional substituent (which, unless otherwise indicated, is preferably not further substituted). For instance, alkyl may be substituted by halo (resulting, for instance, in CF$_3$).

"Substructure" means the chemical structure of the compound and any compounds derived from that chemical structure via the replacement of one or more hydrogen atoms by any other atom (which atom may be bound to other atoms or groups). Replacement, for instance, may be of one ore more, preferably 1 or 2, more preferably 1, hydrogen atoms with an independently selected optional substituent. Encompassed within the definition of "substructure" are materials wherein the substructure forms a fragment of a larger compound, such as a monomer (e.g., containing one or more polymerizable groups), a polymer, or a macromolecule.

"Visible light absorption maximum" means a wavelength in the visible light wavelength range (380 to 760 nm) at which a light absorbance is a maximum. The definition encompasses materials that exhibit absorption maxima outside of the visible light range, such as within the UV region.

The terms "photostable," "photostability," or similar expressions mean that the compound (which may, when measured, be optionally embedded in an ophthalmic device, such as a hydrogel contact lens, and optionally measured either within or outside of a blister pack or a vial) exhibits a loss of absorbance at the visible light absorbance maximum of no more than 20 percent after exposure to light under conditions such as those of the International Conference on Harmonisation (ICH) of Technical Requirements for Registration of Pharmaceuticals for Human Use guideline, Q1B Photostability Testing of New Drug Substances and Products, published on November 1996. Preferably, the exposure is conducted under the ICH Photostability Guideline using an Option 2 light source with an estimated illuminance exposure of $1.5192 \times 10^6$ Lux hours (168.8 hours exposure time) and an estimated ultraviolet irradiation exposure of 259.4 Watt hours/m$^2$ (16.2 hours exposure time), preferably in a photostability chamber that is controlled at 25° C./Amb RH. After exposure, the UV/Vis spectrum of the sample is collected and compared to a sample's spectrum prior to exposure. By way of example, if the absorbance at the visible light absorbance maximum before exposure is 4 absorbance units, and is 2 absorbance units after exposure, then the loss of absorbance is 50 percent. In the invention, the loss of absorbance after exposure is preferably no more than 15 percent, or no more than 10 percent, or no more than 5 percent, or no more than 4 percent, or no more than 3 percent, or no more than 2 percent, or no more than 1 percent, or no more than 0.5 percent, or no more than 0.1 percent.

The term "more photostable than macular pigment" or similar expression means that the compound (which may, when tested, be optionally embedded in an ophthalmic device, such as a hydrogel contact lens, and optionally measured either within or outside of a blister pack) exhibits less loss of absorbance at the visible light absorbance maximum than observed with macular pigment, following exposure to light, for instance under the ICH Photostability Guideline as described above.

The term full width half maximum (FWHM) means the width of the absorbance peak at half its maximum intensity.

Unless otherwise indicated, ratios, percentages, parts, and the like are by weight.

Unless otherwise indicated, numeric ranges, for instance as in "from 2 to 10" or "between 2 and 10" are inclusive of the numbers defining the range (e.g., 2 and 10).

As noted above, in one aspect, the invention provides compounds that substantially mimic the visible light absorbance properties of macular pigment. The compounds are more photostable than macular pigment and may therefore be used in the manufacture of products. For instance, the compounds may be used in ophthalmic devices.

Thus, a compound of the invention may have a visible light absorption maximum that is between 430 and 480 nm and a full width half maximum (FWHM) at the visible light absorption maximum of at least 35 nm and up to 100 nanometers. The compound may be photostable (e.g., when measured according to ICH guideline Q1B). The compound may be more photostable than macular pigment.

The compound may have a visible light absorption maximum that is between 440 nm and 470 nm, or between 445 nm and 465 nm, or between 450 nm and 460 nm, or between 455 nm and 460 nm.

The compound may exhibit a FWHM at the visible light absorption maximum of at least 35 nm, or at least 40 nm, or at least 45 nm, or at least 55 nm, or at least 60 nm, or at least 65 nm. The compound may exhibit a FWHM at the visible light absorption maximum of up to 95 nm, or up to 90 nm, or up to 85 nm, or up to 80 nm, or up to 75 nm, or up to 70 nm. The FWHM at the visible light absorption maximum may be in the range of 35 nm to 100 nm, or 45 nm to 90 nm, or 55 nm to 80 nm, or 60 nm to 75 nm, or 65 nm to 70 nm.

The compound of the invention may exhibit a molar extinction coefficient at the visible light absorption maximum of at least 5000, or at least 5500, or at least 6000, or at least 6500, or at least 7000, or at least 7500.

The compound of the invention may comprise a chromophore having a substructure of formula I:

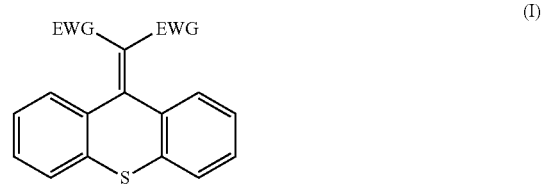

(I)

wherein EWG at each occurrence is independently an electron withdrawing group, and wherein the compound exhibits a visible light absorbance peak in the range of 440 to 480 nm.

EWG may, at each occurrence, be independently cyano, amide, ester, keto, or aldehyde. Preferably, EWG is cyano at each occurrence.

Compounds of the invention may be of formula II:

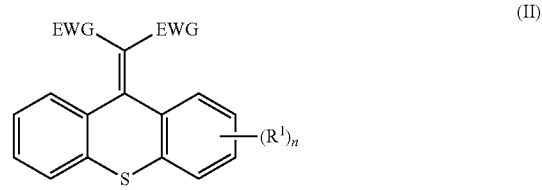

(II)

wherein EWG at each occurrence is independently an electron withdrawing group; n is 1, 2, or 3; and $R^1$ is at each occurrence is independently H, $C_1$-$C_6$ alkyl, $C_1$-$C_6$ alkoxy, $C_1$-$C_6$ thioalkyl, $C_3$-$C_7$ cycloalkyl, aryl, halo, hydroxy, amino, $NR^3R^4$, benzyl, $SO_3H$, or $SO_3M$ (M is a monovalent cation, such as sodium or potassium), or —Y—$P_g$, wherein $R^3$ and $R^4$ are independently H or $C_1$-$C_6$ alkyl, Y is a linking group; and $P_g$ is a polymerizable group. Preferably, the compound contains 0, 1, or 2-Y—$P_g$ groups (that may or may not be the same). If n in formula II is 2 or 3, the R¹ groups may be located at any ring substitutable position.

Compounds of formula II may include compounds of formula II-1, which are compounds of formula II wherein R¹ at each occurrence is independently H or $C_1$-$C_6$ alkyl (preferably ethyl or methyl).

Chomophores of formula II may include compounds of formula II-2, which are compounds of formula II wherein n is 1 and R¹ is Y—$P_g$.

Compounds of formulae II and II-2 may include compounds of formula II-3, which are compounds of formula II or II-2 wherein $P_g$ (a polymerizable group) at each occurrence independently comprises styryl, vinyl carbonate, vinyl ether, vinyl carbamate, N-vinyl lactam, N-vinylamide, (meth)acrylate, or (meth)acrylamide. Preferred polymerizable groups include (meth)acrylate or (meth)acrylamide. A more preferred polymerizable group is methacrylate.

Compounds of formulae II, II-2, and II-3 may include compounds of formula II-4, which are compounds of formula II, II-2, or II-3 wherein Y (a linking group) at each occurrence is independently alkylene, cycloalkylene, heterocycloalkylene, arylene (e.g., phenylene), heteroarylene, oxaalkylene, alkylene-amide-alkylene, alkylene-amine-alkylene, or combinations of any of the foregoing groups. Preferred linking groups include $C_1$-$C_8$ alkylene (e.g., ethylene or propylene), $C_1$-$C_8$ oxaalkylene, $C_1$-$C_8$ alkylene-amide-$C_1$-$C_8$ alkylene, and $C_1$-$C_8$ alkylene-amine-$C_1$-$C_8$ alkylene. Particularly preferred is $C_1$-$C_8$ oxaalkylene, or $C_2$-$C_4$ oxaalkylene, or oxaethylene (—O—$CH_2CH_2$—).

Compounds of formulae II, II-1, II-2, II-3, and II-4, may include compounds of formula II-5, which are compounds of formula II, II-1, II-2, II-3, or II-4 wherein EWG at each occurrence is independently cyano, amide, ester, keto, or aldehyde. EWG at each occurrence may be cyano.

Compounds of formulae II, II-1, II-2, II-3, II-4, and II-5 may include compounds of formula II-6, which are compounds of formula II, II-1, II-2, II-3, II-4, or II-5 wherein n is 1 or 2, preferably n is 1.

Compounds of the invention may be of formula III:

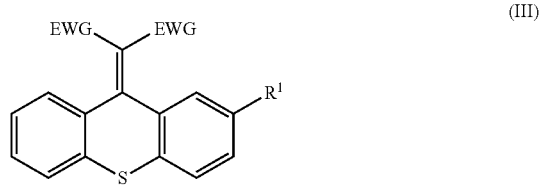

(III)

wherein EWG at each occurrence is independently an electron withdrawing group; and R¹ is H, $C_1$-$C_6$ alkyl, $C_1$-$C_6$ alkoxy, $C_1$-$C_6$ thioalkyl, $C_3$-$C_7$ cycloalkyl, aryl, halo, hydroxy, amino, $NR^3R_4$, benzyl, $SO_3H$, or $SO_3M$ (M is a monovalent cation, such as sodium or potassium), or Y—$P_g$, wherein $R^3$ and $R^4$ are independently H or $C_1$-$C_6$ alkyl, Y is a linking group; and $P_g$ is a polymerizable group.

Compounds of formula III may include compounds of formula III-1, which are compounds of formula III wherein R¹ is H or $C_1$-$C_6$ alkyl (preferably ethyl or methyl).

Chomophores of formula III may include compounds of formula III-2, which are compounds of formula III wherein R¹ is Y—$P_g$.

Compounds of formulae III and III-2 may include compounds of formula III-3, which are compounds of formula III or III-2 wherein $P_g$ (a polymerizable group) comprises styryl, vinyl carbonate, vinyl ether, vinyl carbamate, N-vinyl lactam, N-vinylamide, (meth)acrylate, or (meth)acrylamide. Preferred polymerizable groups include (meth)acrylate or (meth)acrylamide. A more preferred polymerizable group is methacrylate.

Compounds of formulae III, III-2, and III-3 may include compounds of formula III-4, which are compounds of formula III, III-2, or III-3 wherein Y (a linking group) is alkylene, cycloalkylene, heterocycloalkylene, arylene (e.g., phenylene), heteroarylene, oxaalkylene, alkylene-amide-alkylene, alkylene-amine-alkylene, or combinations of any of the foregoing groups. Preferred linking groups include $C_1$-$C_8$ alkylene (e.g., ethylene or propylene), $C_1$-$C_8$ oxaalkylene, $C_1$-$C_8$ alkylene-amide-$C_1$-$C_8$ alkylene, and $C_1$-$C_8$ alkylene-amine-$C_1$-$C_8$ alkylene. Particularly preferred is $C_1$-$C_8$ oxaalkylene, or $C_2$-$C_4$ oxaalkylene, or oxaethylene (—O—$CH_2CH_2$—).

Compounds of formulae III, III-1, 111-2, 111-3, and III-4, may include compounds of formula III-5, which are compounds of formula III, III-1, III-2, III-3, or III-4 wherein EWG at each occurrence is independently cyano, amide, ester, keto, or aldehyde. EWG at each occurrence may be cyano.

Specific examples of compounds of the invention are shown in Table A.

TABLE A

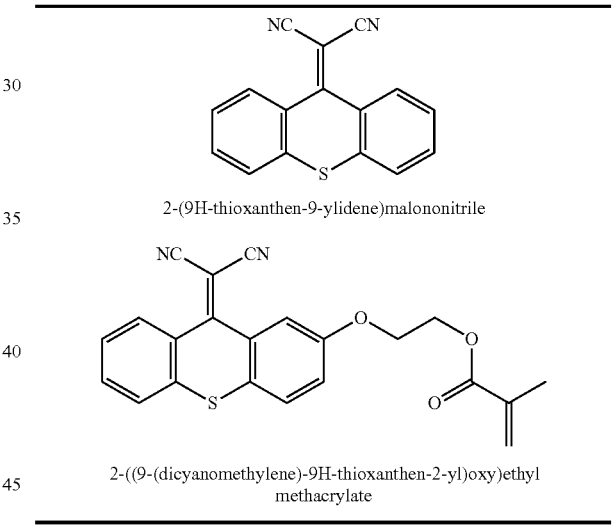

2-(9H-thioxanthen-9-ylidene)malononitrile 2-((9-(dicyanomethylene)-9H-thioxanthen-2-yl)oxy)ethyl methacrylate Compounds of the invention may be used in combination with other light absorbing compounds to provide desirable absorption characteristics. For example, preferred compositions may comprise a compound as described above together with a UV absorbing compound. Suitable UV absorbing compounds are known in the art and fall into several classes which include, but are not limited to, benzophenones, benzotriazoles, triazines, substituted acrylonitriles, salicyclic acid derivatives, benzoic acid derivatives, cinnamic acid derivatives, chalcone derivatives, dypnone derivatives, crotonic acid derivatives, or any mixtures thereof. A preferred class of UV absorbing compound is benzotriazoles, such as Norbloc (2-(2'-hydroxy-5-methacrylyloxyethylphenyl)-2H-benzotriazole).

Compounds of the invention may be included in reactive mixtures to form various products, including biomedical devices and ophthalmic devices. The compounds may, for instance, be incorporated within a device, and/or they be coated on the surface of a device. When incorporated within a device, the compounds may generally be added to the reactive mixture from which the device is made and may be present in any amount up to the limit of their solubility. For instance, the compounds may be present at concentration of at least 0.1 percent or at least 2 percent; and up to 10 percent or up to 5 percent, based on the weight percentages of all components in the reactive mixture, excluding diluent. A typical concentration may be in the range of 1 to 5 percent. The upper limit is typically determined by the solubility of the compound with other co-monomers and or diluents in the reactive monomer mix.

Preferably, the compounds of the invention are included in ophthalmic devices. A variety of ophthalmic devices may be prepared, including spectacles, sunglasses, hard contact lenses, soft contact lenses, corneal onlays, corneal inlays, intraocular lenses, or overlay lenses. Preferably, the ophthalmic device is an intraocular lens or a soft contact lens. The soft contact lens may be made from a conventional (non-silicone) hydrogel or from a silicone hydrogel.

Ophthalmic devices of the invention may comprise a free radical reaction product of a reactive mixture containing one or more monomers suitable for making the desired ophthalmic device (also referred to herein as device forming monomers or hydrogel forming monomers), and optional components. When polymerized, the reactive mixture results in formation of a polymeric network of which the ophthalmic device may be comprised. The polymeric network may, for instance, be a hydrogel (e.g., a conventional hydrogel or a silicone hydrogel).

A compound of the invention may be copolymerized with the other components in the reactive mixture, in which case the reactive mixture may, in addition to one or more monomers suitable for making the desired ophthalmic device (and any optional components), also contain one or more of the invention compounds.

Non-limiting examples of polymeric networks in which the invention compound may be incorporated (for instance, as a monomer) are described above and include, for instance, etafilcon, genfilcon, hilafilcon, lenefilcon, nesofilcon, omafilcon, polymacon, vifilcon, acquafilcon, asmofilcon, balafilcon, comfilcon, delefilcon, enfilcon, fanfilcon, formofilcon, galyfilcon, lotrafilcon, narafilcon, riofilcon, samfilcon, senofilcon, somofilcon, and stenfilcon, including all of their variants.

By way of further example, a polymeric network may be made from a reactive mixture comprising one or more of: hydrophilic components, hydrophobic components, silicone-containing components, wetting agents such as polyamides, crosslinking agents, and further components such as diluents and initiators. As discussed above, the reactive mixture may also contain one or more inventive compounds.

Hydrophilic Components

Examples of suitable families of hydrophilic monomers that may be present in the reactive mixture include (meth)acrylates, styrenes, vinyl ethers, (meth)acrylamides, N-vinyl lactams, N-vinyl amides, N-vinyl imides, N-vinyl ureas, O-vinyl carbamates, O-vinyl carbonates, other hydrophilic vinyl compounds, and mixtures thereof.

Non-limiting examples of hydrophilic (meth)acrylate and (meth)acrylamide monomers include: acrylamide, N-isopropyl acrylamide, N,N-dimethylaminopropyl (meth)acrylamide, N,N-dimethyl acrylamide (DMA), 2-hydroxyethyl methacrylate (HEMA), 2-hydroxypropyl (meth)acrylate, 3-hydroxypropyl (meth)acrylate, 2,3-dihydroxypropyl (meth)acrylate, 2-hydroxybutyl (meth)acrylate, 3-hydroxybutyl (meth)acrylate, 4-hydroxybutyl (meth)acrylate, N-(2-hydroxyethyl) (meth)acrylamide, N,N-bis(2-hydroxyethyl) (meth)acrylamide, N-(2-hydroxypropyl) (meth)acrylamide, N,N-bis(2-hydroxypropyl) (meth)acrylamide, N-(3-hydroxypropyl) (meth)acrylamide, N-(2-hydroxybutyl) (meth)acrylamide, N-(3-hydroxybutyl) (meth)acrylamide, N-(4-hydroxybutyl) (meth)acrylamide, 2-aminoethyl (meth)acrylate, 3-aminopropyl (meth)acrylate, 2-aminopropyl (meth)acrylate, N-2-aminoethyl (meth)acrylamides), N-3-aminopropyl (meth)acrylamide, N-2-aminopropyl (meth)acrylamide, N,N-bis-2-aminoethyl (meth)acrylamides, N,N-bis-3-aminopropyl (meth)acrylamide), N,N-bis-2-aminopropyl (meth)acrylamide, glycerol methacrylate, polyethyleneglycol monomethacrylate, (meth)acrylic acid, vinyl acetate, acrylonitrile, and mixtures thereof.

Hydrophilic monomers may also be ionic, including anionic, cationic, zwitterions, betaines, and mixtures thereof. Non-limiting examples of such charged monomers include (meth)acrylic acid, N-[(ethenyloxy)carbonyl]-o-alanine (VINAL), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT), 1-propanaminium, N,N-dimethyl-N-[3-[(1-oxo-2-propen-1-yl)amino]propyl]-3-sulfo-, inner salt (SBT), 3,5-Dioxa-8-aza-4-phosphaundec-10-en-1-aminium, 4-hydroxy-N,N,N-trimethyl-9-oxo-, inner salt, 4-oxide (9C) (PBT), 2-methacryloyloxyethyl phosphorylcholine, 3-(dimethyl(4-vinylbenzyl)ammonio)propane-1-sulfonate (DMVBAPS), 3-((3-acrylamidopropyl)dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), and methacryloyloxy)propyl)dimethylammonio)propane-1-sulfonate (MAPDAPS).

Non-limiting examples of hydrophilic N-vinyl lactam and N-vinyl amide monomers include: N-vinyl pyrrolidone (NVP), N-vinyl-2-piperidone, N-vinyl-2-caprolactam, N-vinyl-3-methyl-2-caprolactam, N-vinyl-3-methyl-2-piperidone, N-vinyl-4-methyl-2-piperidone, N-vinyl-4-methyl-2-caprolactam, N-vinyl-3-ethyl-2-pyrrolidone, N-vinyl-4,5-dimethyl-2-pyrrolidone, N-vinyl acetamide (NVA), N-vinyl-N-methylacetamide (VMA), N-vinyl-N-ethyl acetamide, N-vinyl-N-ethyl formamide, N-vinyl formamide, N-vinyl-N-methylpropionamide, N-vinyl-N-methyl-2-methylpropionamide, N-vinyl-2-methylpropionamide, N-vinyl-N,N'-dimethylurea, 1-methyl-3-methylene-2-pyrrolidone, 1-methyl-5-methylene-2-pyrrolidone, 5-methyl-3-methylene-2-pyrrolidone; 1-ethyl-5-methylene-2-pyrrolidone, N-methyl-3-methylene-2-pyrrolidone, 5-ethyl-3-methylene-2-pyrrolidone, 1-N-propyl-3-methylene-2-pyrrolidone, 1-N-propyl-5-methylene-2-pyrrolidone, 1-isopropyl-3-methylene-2-pyrrolidone, 1-isopropyl-5-methylene-2-pyrrolidone, N-vinyl-N-ethyl acetamide, N-vinyl-N-ethyl formamide, N-vinyl formamide, N-vinyl isopropylamide, N-vinyl caprolactam, N-vinylimidazole, and mixtures thereof Non-limiting examples of hydrophilic O-vinyl carbamates and O-vinyl carbonates monomers include N-2-hydroxyethyl vinyl carbamate and N-carboxy-β-alanine N-vinyl ester. Further examples of hydrophilic vinyl carbonate or vinyl carbamate monomers are disclosed in U.S. Pat. No. 5,070,215. Hydrophilic oxazolone monomers are disclosed in U.S. Pat. No. 4,910,277.

Other hydrophilic vinyl compounds include ethylene glycol vinyl ether (EGVE), di(ethylene glycol) vinyl ether (DEGVE), allyl alcohol, and 2-ethyl oxazoline.

The hydrophilic monomers may also be macromers or prepolymers of linear or branched poly(ethylene glycol), poly(propylene glycol), or statistically random or block copolymers of ethylene oxide and propylene oxide, having polymerizable moieties such as (meth)acrylates, styrenes, vinyl ethers, (meth)acrylamides, N-vinylamides, and the like. The macromers of these polyethers have one polymerizable group; the prepolymers may have two or more polymerizable groups.

The preferred hydrophilic monomers of the present invention are DMA, NVP, HEMA, VMA, NVA, and mixtures thereof. Preferred hydrophilic monomers include mixtures of DMA and HEMA. Other suitable hydrophilic monomers will be apparent to one skilled in the art.

Generally, there are no particular restrictions with respect to the amount of the hydrophilic monomer present in the reactive monomer mixture. The amount of the hydrophilic monomers may be selected based upon the desired characteristics of the resulting hydrogel, including water content, clarity, wettability, protein uptake, and the like. Wettability may be measured by contact angle, and desirable contact angles are less than about 100°, less than about 80°, and less than about 60°. The hydrophilic monomer may be present in an amount in the range of, for instance, about 0.1 to about 100 weight percent, alternatively in the range of about 1 to about 80 weight percent, alternatively about 5 to about 65 weight percent, alternatively in the range of about 40 to about 60 weight percent, or alternatively about 55 to about 60 weight percent, based on the total weight of the reactive components in the reactive monomer mixture.

Silicone-Containing Components

Silicone-containing components suitable for use in the invention comprise one or more polymerizable compounds, where each compound independently comprises at least one polymerizable group, at least one siloxane group, and one or more linking groups connecting the polymerizable group(s) to the siloxane group(s). The silicone-containing components may, for instance, contain from 1 to 220 siloxane repeat units, such as the groups defined below. The silicone-containing component may also contain at least one fluorine atom.

The silicone-containing component may comprise: one or more polymerizable groups as defined above; one or more optionally repeating siloxane units; and one or more linking groups connecting the polymerizable groups to the siloxane units. The silicone-containing component may comprise: one or more polymerizable groups that are independently a (meth)acrylate, a styryl, a vinyl ether, a (meth)acrylamide, an N-vinyl lactam, an N-vinylamide, an O-vinylcarbamate, an O-vinylcarbonate, a vinyl group, or mixtures of the foregoing; one or more optionally repeating siloxane units; and one or more linking groups connecting the polymerizable groups to the siloxane units.

The silicone-containing component may comprise: one or more polymerizable groups that are independently a (meth)acrylate, a (meth)acrylamide, an N-vinyl lactam, an N-vinylamide, a styryl, or mixtures of the foregoing; one or more optionally repeating siloxane units; and one or more linking groups connecting the polymerizable groups to the siloxane units.

The silicone-containing component may comprise: one or more polymerizable groups that are independently a (meth) acrylate, a (meth)acrylamide, or mixtures of the foregoing; one or more optionally repeating siloxane units; and one or more linking groups connecting the polymerizable groups to the siloxane units.

The silicone-containing component may comprise one or more polymerizable compounds of Formula A:

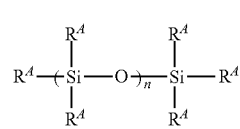

Formula A wherein:

at least one $R^A$ is a group of formula $R_g$-L- wherein $R_g$ is a polymerizable group and L is a linking group, and the remaining $R^A$ are each independently:

(a) $R_g$-L-, (b) $C_1$-$C_{16}$ alkyl optionally substituted with one or more hydroxy, amino, amido, oxa, carboxy, alkyl carboxy, carbonyl, alkoxy, amido, carbamate, carbonate, halo, phenyl, benzyl, or combinations thereof, (c) $C_3$-$C_{12}$ cycloalkyl optionally substituted with one or more alkyl, hydroxy, amino, amido, oxa, carbonyl, alkoxy, amido, carbamate, carbonate, halo, phenyl, benzyl, or combinations thereof, (d) a $C_6$-$C_{14}$ aryl group optionally substituted with one or more alkyl, hydroxy, amino, amido, oxa, carboxy, alkyl carboxy, carbonyl, alkoxy, amido, carbamate, carbonate, halo, phenyl, benzyl, or combinations thereof, (e) halo, (f) alkoxy, cyclic alkoxy, or aryloxy, (g) siloxy, (h) alkyleneoxy-alkyl or alkoxy-alkyleneoxy-alkyl, such as polyethyleneoxyalkyl, polypropyleneoxyalkyl, or poly(ethyleneoxy-co-propyleneoxyalkyl), or (i) a monovalent siloxane chain comprising from 1 to 100 siloxane repeat units optionally substituted with alkyl, alkoxy, hydroxy, amino, oxa, carboxy, alkyl carboxy, alkoxy, amido, carbamate, halo or combinations thereof; and n is from 0 to 500 or from 0 to 200, or from 0 to 100, or from 0 to 20, where it is understood that when n is other than 0, n is a distribution having a mode equal to a stated value. When n is 2 or more, the SiO units may carry the same or different $R^A$ substituents and if different $R^A$ substituents are present, the n groups may be in random or block configuration.

In Formula A, three $R^A$ may each comprise a polymerizable group, alternatively two $R^A$ may each comprise a polymerizable group, or alternatively one $R^A$ may comprise a polymerizable group.

Examples of silicone-containing components suitable for use in the invention include, but are not limited to, compounds listed in Table B. Where the compounds in Table B contain polysiloxane groups, the number of SiO repeat units in such compounds, unless otherwise indicated, is preferably from 3 to 100, more preferably from 3 to 40, or still more preferably from 3 to 20.

TABLE B 1. mono-methacryloxypropyl terminated mono-n-butyl terminated polydimethylsiloxanes (mPDMS) (preferably containing from 3 to 15 SiO repeating units)
2. mono-acryloxypropyl terminated mono-n-butyl terminated polydimethylsiloxane
3. mono(meth)acryloxypropyl terminated mono-n-methyl terminated polydimethylsiloxane
4. mono(meth)acryloxypropyl terminated mono-n-butyl terminated polydiethylsiloxane
5. mono(meth)acryloxypropyl terminated mono-n-methyl terminated polydiethylsiloxane
6. mono(meth)acrylamidoalkylpolydialkylsiloxanes
7. mono(meth)acryloxyalkyl terminated mono-alkyl polydiarylsiloxanes
8. 3-methacryloxypropyltris(trimethylsiloxy)silane (TRIS)
9. 3-methacryloxypropylbis(trimethylsiloxy)methylsilane
10. 3-methacryloxypropylpentamethyl disiloxane
11. mono(meth)acrylamidoalkylpolydialkylsiloxanes
12. mono(meth)acrylamidoalkyl polydimethylsiloxanes
13. N-(2,3-dihydroxypropane)-N'-(propyl tetra(dimethylsiloxy) dimethylbutylsilane)acrylamide
14. N-[3-tris(trimethylsiloxy)silyl]-propyl acrylamide (TRIS-Am)
15. 2-hydroxy-3-[3-methyl-3,3-di(trimethylsiloxy)silylpropoxy]-propyl methacrylate (SiMAA)
16. 2-hydroxy-3-methacryloxypropyloxypropyl-tris(trimethylsiloxy)silane 17. 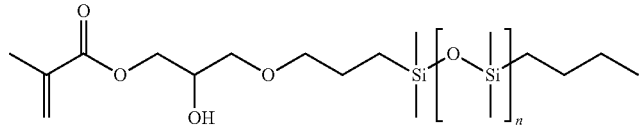

mono-(2-hydroxy-3-methacryloxypropyloxy)-propyl terminated mono-n-butyl terminated polydimethylsiloxanes (OH-mPDMS) (containing from 4 to 30, or from 4 to 20, or from 4 to 15 SiO repeat units)

18. 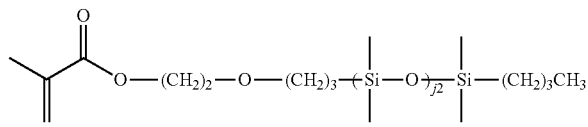

19. 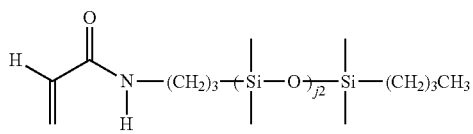

20. 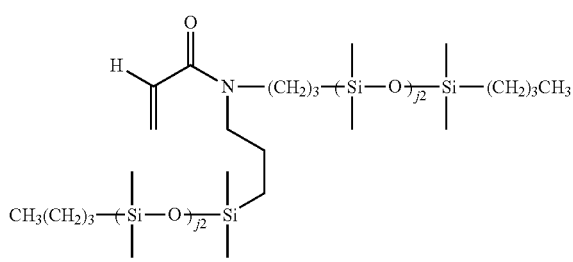

21. 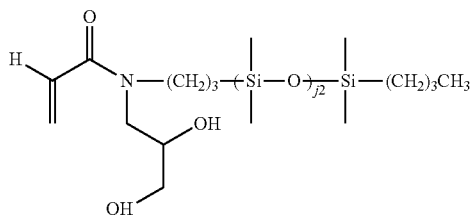

22. 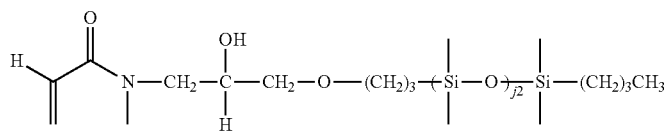

23. 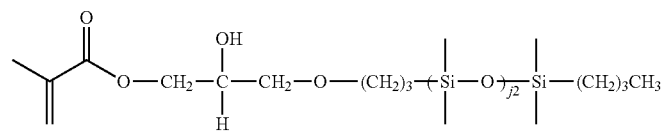

TABLE B-continued

24

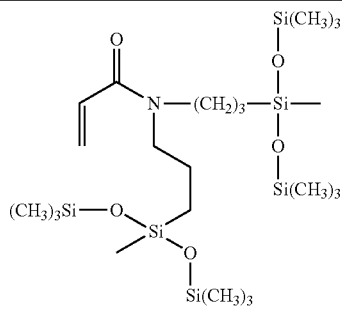

Additional non-limiting examples of suitable silicone-containing components are listed in Table C. Unless otherwise indicated, j2 where applicable is preferably from 1 to 100, more preferably from 3 to 40, or still more preferably from 3 to 15. In compounds containing j1 and j2, the sum of j1 and j2 is preferably from 2 to 100, more preferably from 3 to 40, or still more preferably from 3 to 15.

TABLE C

25

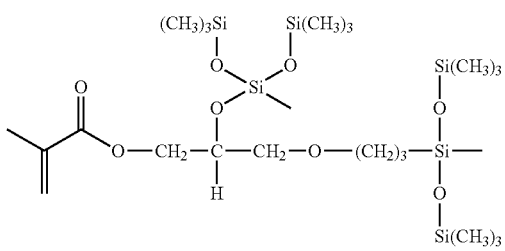

26

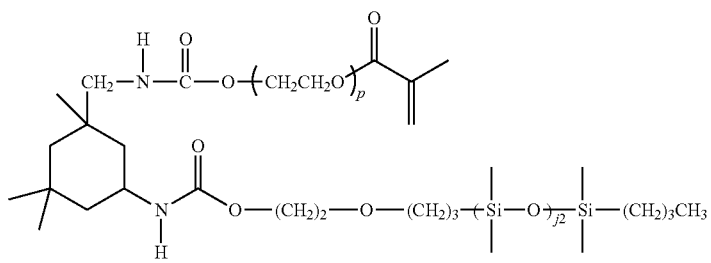

p is 1 to 10

27

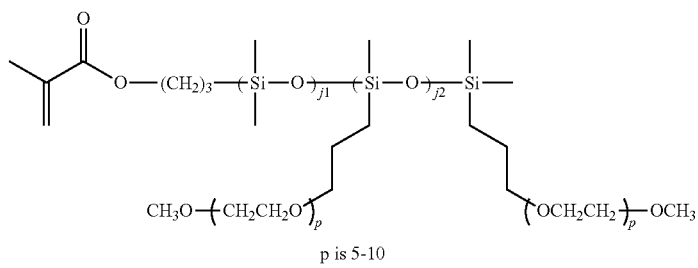

p is 5-10

28

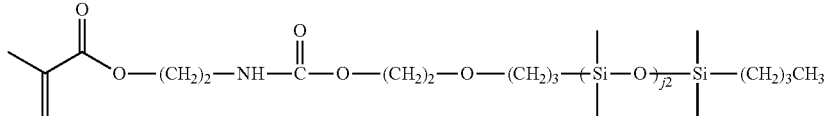

TABLE C-continued
| 29 | 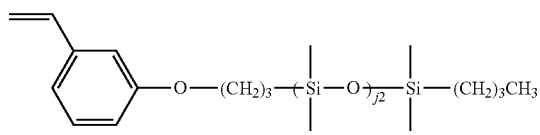 |
|---|---|
| 30 | 1,3-bis[4-(vinyloxycarbonyloxy)but-1-yl]tetramethyl-disiloxane |
| 31 | 3-(vinyloxycarbonylthio) propyl-[tris(trimethylsiloxy)silane] |
| 32 | 3-[tris(trimethylsiloxy)silyl] propyl allyl carbamate |
| 33 | 3-[tris(trimethylsiloxy)silyl] propyl vinyl carbamate |
| 34 | tris(trimethylsiloxy)silylstyrene (Styryl-TRIS) |
35 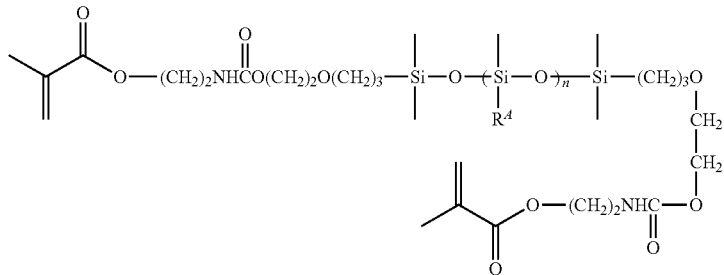
$R^A = CH_3$ (a) or $CH_2CH_2CF_3$ (b) or $CH_2-(CH_2)_2-[OCH_2CH_2]_{1-10}-OCH_3$ (c); $a + b + c = n$
36 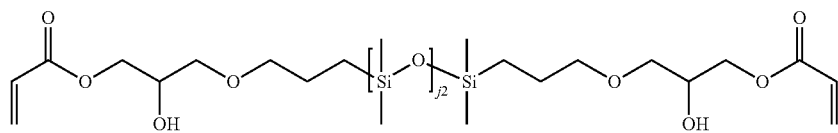
37 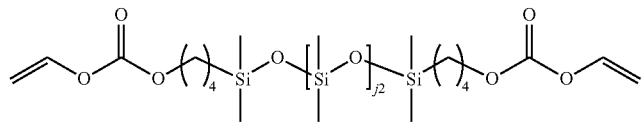
38 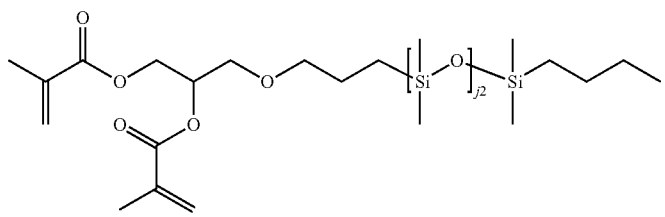
39 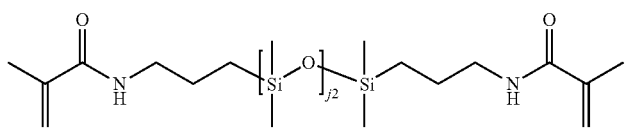
40 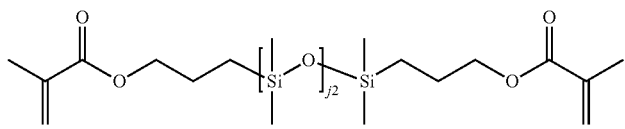

TABLE C-continued

41

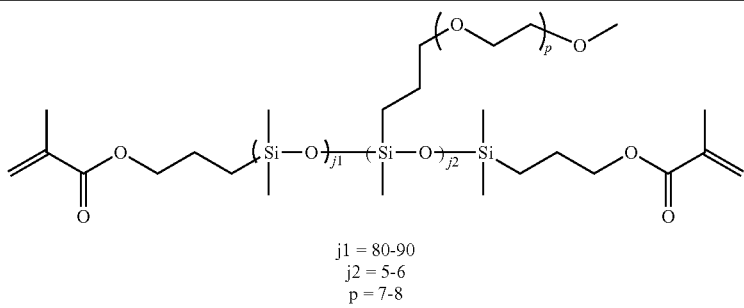

j1 = 80-90
j2 = 5-6
p = 7-8

Mixtures of silicone-containing components may be used. By way of example, suitable mixtures may include, but are not limited to: a mixture of mono-(2-hydroxy-3-methacryloxypropyloxy)-propyl terminated mono-n-butyl terminated polydimethylsiloxane (OH-mPDMS) having different molecular weights, such as a mixture of OH-mPDMS containing 4 and 15 SiO repeat units; a mixture of OH-mPDMS with different molecular weights (e.g., containing 4 and 15 repeat SiO repeat units) together with a silicone based crosslinker, such as bis-3-acryloxy-2-hydroxypropyloxypropyl polydimethylsiloxane (ac-PDMS); a mixture of 2-hydroxy-3-[3-methyl-3,3-di(trimethylsiloxy)silylpropoxy]-propyl methacrylate (SiMAA) and mono-methacryloxypropyl terminated mono-n-butyl terminated polydimethylsiloxane (mPDMS), such as mPDMS 1000.

Silicone-containing components for use in the invention may have an average molecular weight of from about 400 to about 4000 daltons.

The silicone containing component(s) may be present in amounts up to about 95 weight %, or from about 10 to about 80 weight %, or from about 20 to about 70 weight %, based upon all reactive components of the reactive mixture (excluding diluents).

Polyamides

The reactive mixture may include at least one polyamide. As used herein, the term "polyamide" refers to polymers and copolymers comprising repeating units containing amide groups. The polyamide may comprise cyclic amide groups, acyclic amide groups and combinations thereof and may be any polyamide known to those of skill in the art. Acyclic polyamides comprise pendant acyclic amide groups and are capable of association with hydroxyl groups. Cyclic polyamides comprise cyclic amide groups and are capable of association with hydroxyl groups.

Examples of suitable acyclic polyamides include polymers and copolymers comprising repeating units of Formulae G1 and G2:

Formula G1

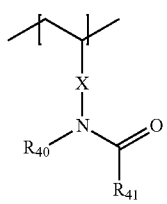

-continued

Formula G2

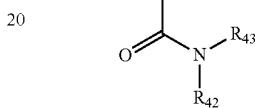

wherein X is a direct bond, —(CO)—, or —(CONHR$_{44}$)—, wherein R$_{44}$ is a C$_1$ to C$_3$ alkyl group; R$_{40}$ is selected from H, straight or branched, substituted or unsubstituted C$_1$ to C$_4$ alkyl groups; R$_{41}$ is selected from H, straight or branched, substituted or unsubstituted C$_1$ to C$_4$ alkyl groups, amino groups having up to two carbon atoms, amide groups having up to four carbon atoms, and alkoxy groups having up to two carbon groups; R$_{42}$ is selected from H, straight or branched, substituted or unsubstituted C$_1$ to C$_4$ alkyl groups; or methyl, ethoxy, hydroxyethyl, and hydroxymethyl; R$_{43}$ is selected from H, straight or branched, substituted or unsubstituted C$_1$ to C$_4$ alkyl groups; or methyl, ethoxy, hydroxyethyl, and hydroxymethyl; wherein the number of carbon atoms in R$_{40}$ and R$_{41}$ taken together is 8 or less, including 7, 6, 5, 4, 3, or less; and wherein the number of carbon atoms in R$_{42}$ and R$_{43}$ taken together is 8 or less, including 7, 6, 5, 4, 3, or less. The number of carbon atoms in R$_{40}$ and R$_{41}$ taken together may be 6 or less or 4 or less. The number of carbon atoms in R$_{42}$ and R$_{43}$ taken together may be 6 or less. As used herein substituted alkyl groups include alkyl groups substituted with an amine, amide, ether, hydroxyl, carbonyl or carboxy groups or combinations thereof.

R$_{40}$ and R$_{41}$ may be independently selected from H, substituted or unsubstituted C$_1$ to C$_2$ alkyl groups. X may be a direct bond, and R$_{40}$ and R$_{41}$ may be independently selected from H, substituted or unsubstituted C$_1$ to C$_2$ alkyl groups. R$_{42}$ and R$_{43}$ can be independently selected from H, substituted or unsubstituted C$_1$ to C$_2$ alkyl groups, methyl, ethoxy, hydroxyethyl, and hydroxymethyl.

The acyclic polyamides of the present invention may comprise a majority of the repeating units of Formula LV or Formula LVI, or the acyclic polyamides can comprise at least 50 mole percent of the repeating unit of Formula G or Formula G1, including at least 70 mole percent, and at least 80 mole percent. Specific examples of repeating units of Formula G and Formula G1 include repeating units derived from N-vinyl-N-methylacetamide, N-vinylacetamide, N-vinyl-N-methylpropionamide, N-vinyl-N-methyl-2-methylpropionamide, N-vinyl-2-methylpropionamide, N-vinyl-N,N'-dimethylurea, N, N-dimethylacrylamide, methacrylamide, and acyclic amides of Formulae G2 and G3:

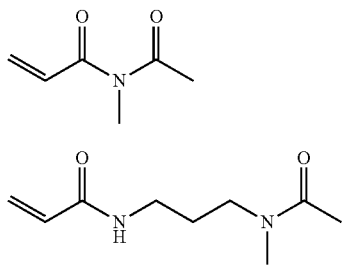

Formula G2

Formula G3

Examples of suitable cyclic amides that can be used to form the cyclic polyamides of include α-lactam, β-lactam, γ-lactam, δ-lactam, and ε-lactam. Examples of suitable cyclic polyamides include polymers and copolymers comprising repeating units of Formula G4:

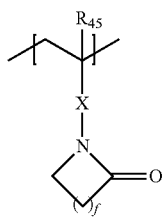

Formula G4 wherein $R_{45}$ is a hydrogen atom or methyl group; wherein f is a number from 1 to 10; wherein X is a direct bond, —(CO)—, or —(CONHR$_{46}$)—, wherein $R_{46}$ is a $C_1$ to $C_3$ alkyl group. In Formula LIX, f may be 8 or less, including 7, 6, 5, 4, 3, 2, or 1. In Formula G4, f may be 6 or less, including 5, 4, 3, 2, or 1. In Formula G4, f may be from 2 to 8, including 2, 3, 4, 5, 6, 7, or 8. In Formula LIX, f may be 2 or 3. When X is a direct bond, f may be 2. In such instances, the cyclic polyamide may be polyvinylpyrrolidone (PVP).

The cyclic polyamides of the present invention may comprise 50 mole percent or more of the repeating unit of Formula G4, or the cyclic polyamides can comprise at least 50 mole percent of the repeating unit of Formula G4, including at least 70 mole percent, and at least 80 mole percent.

The polyamides may also be copolymers comprising repeating units of both cyclic and acyclic amides. Additional repeating units may be formed from monomers selected from hydroxyalkyl(meth)acrylates, alkyl(meth)acrylates, other hydrophilic monomers and siloxane substituted (meth)acrylates. Any of the monomers listed as suitable hydrophilic monomers may be used as co-monomers to form the additional repeating units. Specific examples of additional monomers which may be used to form polyamides include 2-hydroxyethyl (meth)acrylate, vinyl acetate, acrylonitrile, hydroxypropyl (meth)acrylate, methyl (meth)acrylate and hydroxybutyl (meth)acrylate, dihydroxypropyl (meth)acrylate, polyethylene glycol mono(meth)acrylate, and the like and mixtures thereof. Ionic monomers may also be included. Examples of ionic monomers include (meth)acrylic acid, N-[(ethenyloxy)carbonyl]-β-alanine (VINAL, CAS #148969-96-4), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT, carboxybetaine; CAS 79704-35-1), 1-propanaminium, N,N-dimethyl-N-[3-[(1-oxo-2-propen-1-yl)amino]propyl]-3-sulfo-, inner salt (SBT, sulfobetaine, CAS 80293-60-3), 3,5-Dioxa-8-aza-4-phosphaundec-10-en-1-aminium, 4-hydroxy-N,N,N-trimethyl-9-oxo-, inner salt, 4-oxide (9C) (PBT, phosphobetaine, CAS 163674-35-9,2-methacryloyloxyethyl phosphorylcholine, 3-(dimethyl(4-vinylbenzyl)ammonio) propane-1-sulfonate (DMVBAPS), 3-((3-acrylamidopropyl)dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), methacryloyloxy)propyl)dimethylammonio)propane-1-sulfonate (MAPDAPS).

The reactive monomer mixture may comprise both an acyclic polyamide and a cyclic polyamide or copolymers thereof. The acyclic polyamide can be any of those acyclic polyamides described herein or copolymers thereof, and the cyclic polyamide can be any of those cyclic polyamides described herein or copolymers thereof. The polyamide may be selected from the group polyvinylpyrrolidone (PVP), polyvinylmethyacetamide (PVMA), polydimethylacrylamide (PDMA), polyvinylacetamide (PNVA), poly(hydroxyethyl(meth)acrylamide), polyacrylamide, and copolymers and mixtures thereof. The polyamide may be a mixture of PVP (e.g., PVP K90) and PVMA (e.g., having a Mw of about 570 KDa).

The total amount of all polyamides in the reactive mixture may be in the range of between 1 weight percent and about 35 weight percent, including in the range of about 1 weight percent to about 15 weight percent, and in the range of about 5 weight percent to about 15 weight percent, in all cases, based on the total weight of the reactive components of the reactive monomer mixture.

Without intending to be bound by theory, when used with a silicone hydrogel, the polyamide functions as an internal wetting agent. The polyamides of the present invention may be non-polymerizable, and in this case, are incorporated into the silicone hydrogels as semi-interpenetrating networks. The polyamides are entrapped or physically retained within the silicone hydrogels. Alternatively, the polyamides of the present invention may be polymerizable, for example as polyamide macromers or prepolymers, and in this case, are covalently incorporated into the silicone hydrogels. Mixtures of polymerizable and non-polymerizable polyamides may also be used.

When the polyamides are incorporated into the reactive monomer mixture they may have a weight average molecular weight of at least 100,000 daltons; greater than about 150,000; between about 150,000 to about 2,000,000 daltons; between about 300,000 to about 1,800,000 daltons. Higher molecular weight polyamides may be used if they are compatible with the reactive monomer mixture.

Cross-Linking Agents

It is generally desirable to add one or more cross-linking agents, also referred to as cross-linking monomers, multifunctional macromers, and prepolymers, to the reactive mixture. The cross-linking agents may be selected from bifunctional crosslinkers, trifunctional crosslinkers, tetrafunctional crosslinkers, and mixtures thereof, including silicone-containing and non-silicone containing cross-linking agents. Non-silicone-containing cross-linking agents include ethylene glycol dimethacrylate (EGDMA), tetraethylene glycol dimethacrylate (TEGDMA), trimethylolpropane trimethacrylate (TMPTMA), triallyl cyanurate (TAC), glycerol trimethacrylate, methacryloxyethyl vinylcarbonate (HEMAVc), allylmethacrylate, methylene bisacrylamide (MBA), and polyethylene glycol dimethacrylate wherein the polyethylene glycol has a molecular weight up to about 5000 Daltons. The cross-linking agents are used in the usual amounts, e.g., from about 0.000415 to about 0.0156 mole per 100 grams of reactive Formulas in the reactive mixture. Alternatively, if the hydrophilic monomers and/or the silicone-containing components are multifunctional by molecular design or because of impurities, the addition of a cross-linking agent to the reactive mixture is optional. Examples of hydrophilic monomers and macromers which can act as the cross-linking agents and when present do not require the addition of an additional cross-linking agent to the reactive mixture include (meth)acrylate and (meth)acrylamide end-capped polyethers. Other cross-linking agents will be known to one skilled in the art and may be used to make the silicone hydrogel of the present invention.

It may be desirable to select crosslinking agents with similar reactivity to one or more of the other reactive components in the formulation. In some cases, it may be desirable to select a mixture of crosslinking agents with different reactivity in order to control some physical, mechanical or biological property of the resulting silicone hydrogel. The structure and morphology of the silicone hydrogel may also be influenced by the diluent(s) and cure conditions used.

Multifunctional silicone-containing components, including macromers, cross-linking agents, and prepolymers, may also be included to further increase the modulus and retain tensile strength. The silicone containing cross-linking agents may be used alone or in combination with other cross-linking agents. An example of a silicone containing component which can act as a cross-linking agent and, when present, does not require the addition of a crosslinking monomer to the reactive mixture includes α, ω-bismethacryloxypropyl polydimethylsiloxane. Another example is bis-3-acryloxy-2-hydroxypropyloxypropyl polydimethylsiloxane (ac-PDMS).

Cross-linking agents that have rigid chemical structures and polymerizable groups that undergo free radical polymerization may also be used. Non-limiting examples of suitable rigid structures include cross-linking agents comprising phenyl and benzyl ring, such are 1,4-phenylene diacrylate, 1,4-phenylene dimethacrylate, 2,2-bis(4-methacryloxyphenyl)-propane, 2,2-bis[4-(2-acryloxyethoxy)phenyl]propane, 2,2-bis[4-(2-hydroxy-3-methacryloxypropoxy)-phenyl]propane, and 4-vinylbenzyl methacrylate, and combinations thereof. Rigid crosslinking agents may be included in amounts between about 0.5 and about 15, or 2-10, 3-7 based upon the total weight of all of the reactive components. The physical and mechanical properties of the silicone hydrogels of the present invention may be optimized for a particular use by adjusting the components in the reactive mixture.

Non-limiting examples of silicone cross-linking agents also include the multi-functional silicone-containing components described in Table D above.

Further Constituents

The reactive mixture may contain additional components such as, but not limited to, diluents, initiators, UV absorbers, visible light absorbers, photochromic compounds, pharmaceuticals, nutraceuticals, antimicrobial substances, tints, pigments, copolymerizable dyes, nonpolymerizable dyes, release agents, and combinations thereof.

Classes of suitable diluents for silicone hydrogel reactive mixtures include alcohols having 2 to 20 carbon atoms, amides having 10 to 20 carbon atoms derived from primary amines and carboxylic acids having 8 to 20 carbon atoms. The diluents may be primary, secondary, and tertiary alcohols.

Generally, the reactive components are mixed in a diluent to form a reactive mixture. Suitable diluents are known in the art. For silicone hydrogels, suitable diluents are disclosed in WO 03/022321 and U.S. Pat. No. 6,020,445, the disclosure of which is incorporated herein by reference. Classes of suitable diluents for silicone hydrogel reactive mixtures include alcohols having 2 to 20 carbons, amides having 10 to 20 carbon atoms derived from primary amines, and carboxylic acids having 8 to 20 carbon atoms. Primary and tertiary alcohols may be used. Preferred classes include alcohols having 5 to 20 carbons and carboxylic acids having 10 to 20 carbon atoms. Specific diluents which may be used include 1-ethoxy-2-propanol, diisopropylaminoethanol, isopropanol, 3,7-dimethyl-3-octanol, 1-decanol, 1-dodecanol, 1-octanol, 1-pentanol, 2-pentanol, 1-hexanol, 2-hexanol, 2-octanol, 3-methyl-3-pentanol, tert-amyl alcohol, tert-butanol, 2-butanol, 1-butanol, 2-methyl-2-pentanol, 2-propanol, 1-propanol, ethanol, 2-ethyl-1-butanol, (3-acetoxy-2-hydroxypropyloxy)-propylbis(trimethylsiloxy) methylsilane, 1-tert-butoxy-2-propanol, 3,3-dimethyl-2-butanol, tert-butoxyethanol, 2-octyl-1-dodecanol, decanoic acid, octanoic acid, dodecanoic acid, 2-(diisopropylamino) ethanol mixtures thereof and the like. Examples of amide diluents include N,N-dimethyl propionamide and dimethyl acetamide.

Preferred diluents include 3,7-dimethyl-3-octanol, 1-dodecanol, 1-decanol, 1-octanol, 1-pentanol, 1-hexanol, 2-hexanol, 2-octanol, 3-methyl-3-pentanol, 2-pentanol, t-amyl alcohol, tert-butanol, 2-butanol, 1-butanol, 2-methyl-2-pentanol, 2-ethyl-1-butanol, ethanol, 3,3-dimethyl-2-butanol, 2-octyl-1-dodecanol, decanoic acid, octanoic acid, dodecanoic acid, mixtures thereof and the like.

More preferred diluents include 3,7-dimethyl-3-octanol, 1-dodecanol, 1-decanol, 1-octanol, 1-pentanol, 1-hexanol, 2-hexanol, 2-octanol, 1-dodecanol, 3-methyl-3-pentanol, 1-pentanol, 2-pentanol, t-amyl alcohol, tert-butanol, 2-butanol, 1-butanol, 2-methyl-2-pentanol, 2-ethyl-1-butanol, 3,3-dimethyl-2-butanol, 2-octyl-1-dodecanol, mixtures thereof and the like. If a diluent is present, generally there are no particular restrictions with respect to the amount of diluent present. When diluent is used, the diluent may be present in an amount in the range of about 2 to about 70 weight percent, including in the range of about 5 to about 50 weight percent, and in the range of about 15 to about 40 weight percent, based on the total weight of the reactive mixtures (including reactive and nonreactive Formulas). Mixtures of diluents may be used.

A polymerization initiator may be used in the reactive mixture. The polymerization initiator may include, for instance, at least one of lauroyl peroxide, benzoyl peroxide, isopropyl percarbonate, azobisisobutyronitrile, and the like, that generate free radicals at moderately elevated temperatures, and photoinitiator systems such as aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphine oxide (Irgacure 819), 2,4,6-trimethylbenzyldiphenyl phosphine oxide and 2,4,6-trimethylbenzoyl diphenylphosphine oxide, benzoin methyl ester and a combination of cam-phorquinone and ethyl 4-(N,N-dimethylamino)benzoate.

Commercially available (from IGM Resins B. V., The Netherlands) visible light initiator systems include Irgacure® 819, Irgacure® 1700, Irgacure® 1800, Irgacure® 819, Irgacure® 1850 and Lucrin® TPO initiator. Commercially available (from IGM Resins B.V.) UV photoinitiators include Darocur® 1173 and Darocur® 2959. These and other photoinitiators which may be used are disclosed in Volume III, Photoinitiators for Free Radical Cationic & Anionic Photopolymerization, 2nd Edition by J. V. Crivello & K. Dietliker; edited by G. Bradley; John Wiley and Sons; New York; 1998. The initiator is used in the reactive mixture in effective amounts to initiate photopolymerization of the reactive mixture, e.g., from about 0.1 to about 2 parts by weight per 100 parts of reactive monomer mixture. Polymerization of the reactive mixture can be initiated using the appropriate choice of heat or visible or ultraviolet light or other means depending on the polymerization initiator used. Alternatively, initiation can be conducted using e-beam without a photoinitiator. However, when a photoinitiator is used, the preferred initiators are bisacylphosphine oxides, such as bis(2,4,6-tri-methylbenzoyl)-phenyl phosphine oxide (Irgacure® 819) or a combination of 1-hydroxycyclohexyl phenyl ketone and bis(2,6-dimethoxybenzoyl)-2,4-4-trimethylpentyl phosphine oxide (DMBAPO).

The reactive mixture for making the ophthalmic devices of the invention may comprise, in addition to an invention compound, any of the polymerizable compounds and optional components described above.

The reactive mixture may comprise: an invention compound, such as a compound of formula I, and a hydrophilic component.

The reactive mixture may comprise: an invention compound, such as a compound of formula I, and a hydrophilic component selected from DMA, NVP, HEMA, VMA, NVA, methacrylic acid, and mixtures thereof. Preferred are mixtures of HEMA and methacrylic acid.

The reactive mixture may comprise: an invention compound, such as a compound of formula I, a hydrophilic component, and a silicone-containing component.

The reactive mixture may comprise: an invention compound, such as a compound of formula I, a hydrophilic component selected from DMA, HEMA and mixtures thereof, a silicone-containing component selected from 2-hydroxy-3-[3-methyl-3,3-di(trimethylsiloxy)silylpropoxy]-propyl methacrylate (SiMAA), mono-methacryloxypropyl terminated mono-n-butyl terminated polydimethylsiloxane (mPDMS), mono-(2-hydroxy-3-methacryloxypropyl)-propyl ether terminated mono-n-butyl terminated polydimethylsiloxane (OH-mPDMS), and mixtures thereof, and a wetting agent (preferably PVP or PVMA). For the hydrophilic component, mixtures of DMA and HEMA are preferred. For the silicone containing component, mixtures of SiMAA and mPDMS are preferred.

The reactive mixture may comprise: an invention compound, such as a compound of formula I, a hydrophilic component comprising a mixture of DMA and HEMA; a silicone-containing component comprising a mixture of OH-mPDMS having from 2 to 20 repeat units (preferably a mixture of 4 and 15 repeat units). Preferably, the reactive mixture further comprises a silicone-containing crosslinker, such as ac-PDMS. Also preferably, the reactive mixture contains a wetting agent (preferably DMA, PVP, PVMA or mixtures thereof).

The reactive mixture may comprise: an invention compound, such as a compound of formula I; between about 1 and about 15 wt % at least one polyamide (e.g., an acyclic polyamide, a cyclic polyamide, or mixtures thereof); at least one first mono-functional, hydroxyl substituted poly(disubstituted siloxane) having 4 to 8 siloxane repeating units (e.g., OH-mPDMS where n is 4 to 8, preferably n is 4); at least one second hydroxyl substituted poly(disubstituted siloxane) that is a mono-functional hydroxyl substituted poly(disubstituted siloxane)s having 10 to 200 or 10-100 or 10-50 or 10-20 siloxane repeating units (e.g., OH-mPDMS where n is 10 to 200 or 10-100 or 10-50 or 10-20, preferably n is 15); about 5 to about 35 wt % of at least one hydrophilic monomer; and optionally a multifunctional hydroxyl substituted poly(disubstituted siloxane)s having 10 to 200, or 10 to 100 siloxane repeating units (e.g., ac-PDMS). Preferably, the first mono-functional, hydroxyl substituted poly(disubstituted siloxane) and the second hydroxyl substituted poly(disubstituted siloxane) are present in concentrations to provide a ratio of weight percent of the first mono-functional, hydroxyl substituted poly(disubstituted siloxane) to weight percent of the second hydroxyl substituted poly(disubstituted siloxane) of 0.4-1.3, or 0.4-1.0.

The foregoing reactive mixtures may contain optional ingredients such as, but not limited to, one or more initiators, internal wetting agents, crosslinkers, other UV or HEV absorbers, and diluents.

Curing of Hydrogels and Manufacture of Lens

The reactive mixtures may be formed by any of the methods known in the art, such as shaking or stirring, and used to form polymeric articles or devices by known methods. The reactive components are mixed together either with or without a diluent to form the reactive mixture.

For example, ophthalmic devices may be prepared by mixing reactive components, and, optionally, diluent(s), with a polymerization initiator and curing by appropriate conditions to form a product that can be subsequently formed into the appropriate shape by lathing, cutting, and the like. Alternatively, the reactive mixture may be placed in a mold and subsequently cured into the appropriate article.

A method of making a molded ophthalmic device, such as a silicone hydrogel contact lens, may comprise: preparing a reactive monomer mixture; transferring the reactive monomer mixture onto a first mold; placing a second mold on top the first mold filled with the reactive monomer mixture; and curing the reactive monomer mixture by free radical copolymerization to form the silicone hydrogel in the shape of a contact lens.

The reactive mixture may be cured via any known process for molding the reactive mixture in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197,266. The contact lenses of this invention may be formed by the direct molding of the silicone hydrogels, which is economical, and enables precise control over the final shape of the hydrated lens. For this method, the reactive mixture is placed in a mold having the shape of the final desired silicone hydrogel and the reactive mixture is subjected to conditions whereby the monomers polymerize, thereby producing a polymer in the approximate shape of the final desired product.

After curing, the lens may be subjected to extraction to remove unreacted components and release the lens from the lens mold. The extraction may be done using conventional extraction fluids, such organic solvents, such as alcohols or may be extracted using aqueous solutions.

Aqueous solutions are solutions which comprise water. The aqueous solutions of the present invention may comprise at least about 20 weight percent water, or at least about 50 weight percent water, or at least about 70 weight percent water, or at least about 95 weight percent water. Aqueous solutions may also include additional water soluble Formulas such as inorganic salts or release agents, wetting agents, slip agents, pharmaceutical and nutraceutical Formulas, combinations thereof and the like. Release agents are compounds or mixtures of compounds which, when combined with water, decrease the time required to release a contact lens from a mold, as compared to the time required to release such a lens using an aqueous solution that does not comprise the release agent. The aqueous solutions may not require special handling, such as purification, recycling or special disposal procedures.

Extraction may be accomplished, for example, via immersion of the lens in an aqueous solution or exposing the lens to a flow of an aqueous solution. Extraction may also include, for example, one or more of: heating the aqueous solution; stirring the aqueous solution; increasing the level of release aid in the aqueous solution to a level sufficient to cause release of the lens; mechanical or ultrasonic agitation of the lens; and incorporating at least one leaching or extraction aid in the aqueous solution to a level sufficient to facilitate adequate removal of unreacted components from the lens. The foregoing may be conducted in batch or continuous processes, with or without the addition of heat, agitation or both.

Application of physical agitation may be desired to facilitate leach and release. For example, the lens mold part to which a lens is adhered can be vibrated or caused to move back and forth within an aqueous solution. Other methods may include ultrasonic waves through the aqueous solution.

The lenses may be sterilized by known means such as, but not limited to, autoclaving.

As indicated above, preferred ophthalmic devices are contact lenses, more preferably soft hydrogel contact lenses. The transmission wavelengths and percentages described herein may be measured on various thicknesses of lenses using, for instance, the methodologies described in the Examples. By way of example, a preferred center thickness for measuring transmission spectra in a soft contact lens may be from 80 to 100 microns, or from 90 to 100 microns or from 90 to 95 microns. Typically, the measurement may be made at the center of the lens using, for instance, a 4 nm instrument slit width.

Silicone hydrogel ophthalmic devices (e.g., contact lenses) according to the invention preferably exhibit the following properties. All values are prefaced by "about," and the devices may have any combination of the listed properties. The properties may be determined by methods known to those skilled in the art, for instance as described in United States pre-grant publication US20180037690, which is incorporated herein by reference.

Water concentration %: at least 20%, or at least 25% and up to 80% or up to 70%

Haze: 30% or less, or 10% or less

Advancing dynamic contact angle (Wilhelmy plate method): 100° or less, or 80 or less; or 50° or less Tensile Modulus (psi): 120 or less, or 80 to 120 Oxygen permeability (Dk, barrers): at least 80, or at least 100, or at least 150, or at least 200

Elongation to Break: at least 100 For ionic silicon hydrogels, the following properties may also be preferred (in addition to those recited above):

Lysozyme uptake (µg/lens): at least 100, or at least 150, or at least 500, or at least 700

Polyquaternium 1 (PQ1) uptake (%): 15 or less, or 10 or less, or 5 or less

Compounds of the invention may be used with other products, in addition to ophthalmic devices. For instance, the compounds may be used in windows (e.g., vehicle or building windows), or optical equipment, such as binoculars and cameras, and the like. In such use, the compounds may, for instance, be coated on the surface of the device. To facilitate coating, the compound may be dissolved in a solvent.

Some embodiments of the invention will now be described in detail in the following Examples.

EXAMPLES

Test Methods

Ultraviolet-visible spectra of compounds in solution were measured on a Perkin Elmer Lambda 45, an Agilent Cary 6000i, or an Ocean Optics QE65 PRO (DH-2000-BAL Light Source) UV/VIS scanning spectrometer. The instrument was thermally equilibrated for at least thirty minutes prior to use. For the Perkin Elmer instrument, the scan range was 200-800 nm; the scan speed was 960 nm per minute; the slit width was 4 nm; the mode was set on transmission or absorbance; and baseline correction was selected. For the Cary instrument, the scan range was 200-800 nm; the scan speed was 600 nm/min; the slit width was 2 nm; the mode was transmission or absorbance; and baseline correction was selected. For the Ocean Optics instrument, the scan range was 200-800 nm; the slit width was 10 µm; the mode was transmission or absorbance; and baseline correction was selected. A baseline correction was performed before samples were analyzed using the autozero function.

Ultraviolet-visible spectra of contact lenses formed in part from the claimed compositions were measured on a Perkin Elmer Lambda 45 UV/VIS, an Agilent Cary 6000i, or an Ocean Optics UV/VIS scanning spectrometer using packing solution. The instrument was thermally equilibrated for at least thirty minutes prior to use. Baseline correction was performed using cuvettes containing plastic two-piece lens holders and the same solvents. These two-piece contact lens holders were designed to hold the sample in the quartz cuvette in the location through which the incident light beam traverses. The reference cuvette also contained a two-piece holder. To ensure that the thickness of the samples is constant, all lenses were made using identical molds. The center thickness of the contact lens was measured using an electronic thickness gauge. Reported center thickness and percent transmission spectra are obtained by averaging three individual lens data.

It is important to ensure that the outside surfaces of the cuvette are completely clean and dry and that no air bubbles are present in the cuvette. Repeatability of the measurement is improved when the reference cuvette and its lens holder remain constant and when all samples use the same sample cuvette and its lens holder, making sure that both cuvettes are properly inserted into the instrument.

The following abbreviations will be used throughout the Examples and Figures and have the following meanings:
L: liter(s)
mL: milliliter(s)
Equiv. or eq.: equivalent
kg: kilogram(s)
g: gram(s)
mg: milligram(s)
mol: mole(s)
mmol: millimole(s)
Da: dalton or g/mole
kDa: kilodalton or an atomic mass unit equal to 1,000 daltons
min: minute(s)
μm: micrometer(s)
nm: nanometer(s)
$^1$H NMR: proton nuclear magnetic resonance spectroscopy
UV-VIS: ultraviolet-visible spectroscopy
TLC: thin layer chromatography
BC: back or base curve plastic mold
FC: front curve plastic mold HO-mPDMS (n=15):

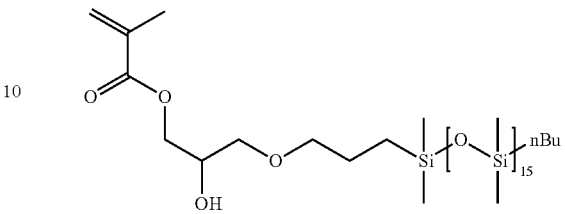

nBu: n-butyl
XLMA: bis-3-methacryloxy-2-hydroxypropyloxypropyl polydimethylsiloxane (Mn=2000 daltons, average n=23 by H$^1$ NMR (CDCl$_3$, 500 MHz) (Shin Etsu)

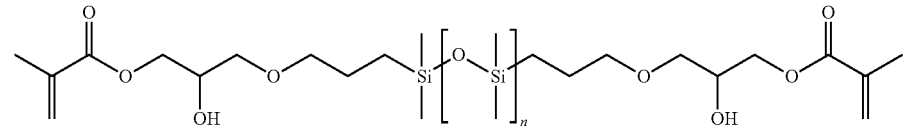

PP: polypropylene which is the homopolymer of propylene
TT: Tuftec which is a hydrogenated styrene butadiene block copolymer (Asahi Kasei Chemicals)
Z: Zeonor which is a polycycloolefin thermoplastic polymer (Nippon Zeon Co Ltd)
DMA: N, N-dimethylacrylamide (Jarchem)
HEMA: 2-hydroxyethyl methacrylate (Bimax)
PVP K90: poly(N-vinylpyrrolidone) (ISP Ashland)
EGDMA: ethylene glycol dimethacrylate (Esstech)
TEGDMA: tetraethylene glycol dimethacrylate (Esstech)
Irgacure or Omnirad 1870: blend of bis(2,6-dimethoxybenzoyl)-2,4,4-trimethyl-pentylphosphineoxide and 1-hydroxycyclohexyl-phenyl-ketone (IGM Resins or BASF or Ciba Specialty Chemicals)
mPDMS: mono-n-butyl terminated monomethacryloxypropyl terminated polydimethylsiloxane (M$_n$=800-1500 daltons) (Gelest)
HO-mPDMS: mono-n-butyl terminated mono-(2-hydroxy-3-methacryloxypropyl)-propyl ether terminated polydimethylsiloxane (Mn=400-1500 g/mol) (Ortec or DSM-Polymer Technology Group)
HO-mPDMS (n=4):

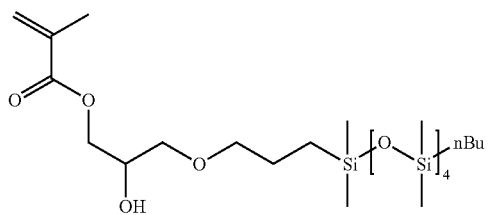

SiMAA: 2-propenoic acid, 2-methyl-2-hydroxy-3-[3-[1,3,3,3-tetramethyl-1-[(trimethylsilyl)oxy]disiloxanyl]propoxy]propyl ester (Toray) or 3-(3-(1,1,1,3,5,5,5-heptamethyltrisiloxan-3-yl)propoxy)-2-hydroxypropyl methacrylate
Norbloc: 2-(2'-hydroxy-5-methacrylyloxyethylphenyl)-2H-benzotriazole (Janssen)
RB247: 1,4-Bis[2-methacryloxyethylamino]-9,10-anthraquinone
TL03 lights: Phillips TLK 40 W/03 bulbs
LED: light emitting diode
D3O: 3,7-dimethyl-3-octanol (Vigon)
3M3P: 3-ethyl-3-pentanol
DIW: deionized water
MeOH: methanol
IPA: isopropyl alcohol
DMF: N,N-dimethylformamide
DMSO: dimethyl sulfoxide
DCM or CH$_2$Cl$_2$: dichloromethane or methylene chloride
DCE: 1,2-dichloroethane
CDCl$_3$: deutrochloroform
PhOH: phenol
H$_2$SO$_4$: sulfuric acid
HCl: hydrochloric acid
pTsOH: p-toluenesulfonic acid
Ac$_2$O: acetic anhydride
Cs$_2$CO$_3$: cesium carbonate
SOCl$_2$: thionyl chloride
NaH: sodium hydride
CPTP: 2-(3-chloropropoxy)tetrahydro-2H-pyran
NaI: sodium iodide
Borate Buffered Packing Solution: 18.52 grams (300 mmol) of boric acid, 3.7 grams (9.7 mmol) of sodium borate decahydrate, and 28 grams (197 mmol) of sodium sulfate were dissolved in enough deionized water to fill a 2-liter volumetric flask.

Example 1—Synthesis of 2-((9-(dicyanomethylene)-9H-thioxanthen-2-yl)oxy)ethyl methacrylate (Compound A) as shown in Scheme 1

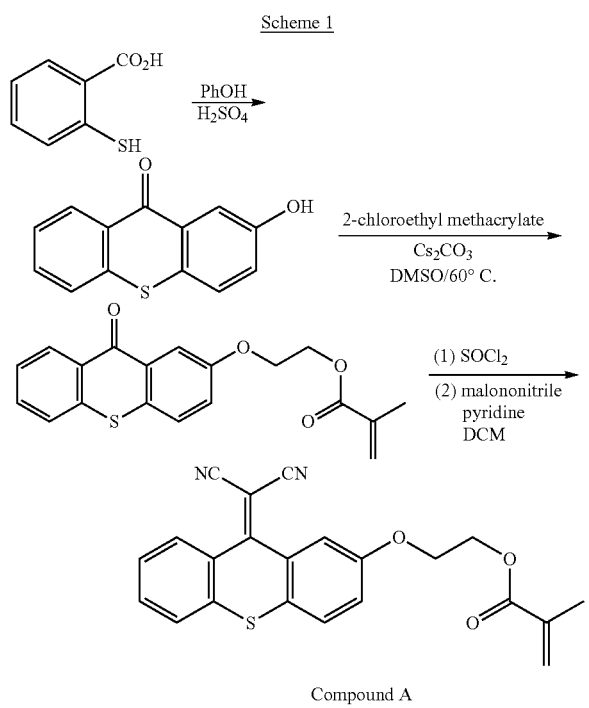

Compound A

Thiosalicylic acid (6.3 grams, ~0.041 mole) was added over 5 minutes to 60 mL of concentrated sulfuric acid while constantly stirring the system. Phenol (18.8 grams, ~5 eq.) was added to the reaction mixture in batches over a 30-minute period during which the temperature increased to 60° C. Once the exotherm ceased, the mixture was heated to 80° C. and then held at that temperature over 2.5 hours with constant stirring. The reaction mixture was slowly added to 600 mL of boiling water while stirring the solution. A bright yellow precipitate formed upon dilution, and the suspension was heated for an additional 10 minutes, after which it was cooled to room temperature. The solids were filtered over a fritted glass funnel. The yellow solids were washed with 3 times with 300 mL of water, dried in a vacuum oven at 50° C., and used "as is" for the next step.

A suspension of 2-hydroxy-9H-thioxanthen-9-one (2.28 grams, 0.01 mole), 2.0 grams of 2-chloroethyl methacrylate (0.0135 mole), and 5.0 grams of cesium carbonate (0.015 mole) in 25 mL of anhydrous DMSO was stirred under a nitrogen atmosphere at 60° C. overnight. The mixture was cooled to room temperature and poured into 300 mL of ethyl acetate. The organics were extracted 3 times with 200 mL of 1% aqueous sodium chloride, after which the volatiles were evaporated under reduced pressure. The residual solids were washed over a fritted glass funnel with hexanes, dried in a vacuum oven at 50° C. and used "as is" for the next step.

2.4 grams of crude 2-(2-methacryloxyethoxy)-9H-thioxanthen-9-one (0.007 mole) were charged into a round bottom flask equipped with a magnetic stir bar and a reflux condenser. The system was placed under a nitrogen atmosphere and thionyl chloride (8 mL, 13.12 grams, 0.111 mole) was added to the flask. The mixture was heated at a gentle reflux for one hour, after which the thionyl chloride was evaporated under reduced pressure. The flask was placed under a nitrogen atmosphere and a solution of 1.39 grams malononitrile (~3 eq.) and 5 grams of pyridine in 20 mL of dichloromethane was added and the mixture stirred at a gentle reflux for an additional two hours.

Once the reaction was complete, the mixture was diluted with 300 mL of ethyl acetate and the organics were extracted with 0.2 N hydrochloric acid, followed by washing 2 times with 300 mL of water. The product was isolated as an orange solid after chromatography over silica gel using methylene chloride and acetone. Compound A: $^1$H NMR (500 MHz, CDCl$_3$) δ 1.92 (3H, bs, CH$_3$), 4.31 (1H, t, J=4.0 Hz), 4.51 (1H, t, 4.5 Hz), 5.56 (1H, bs, vinylic), 6.12 (1H, bs, vinylic), 7.13-8.11 (6H, ArH).

Figure 2:
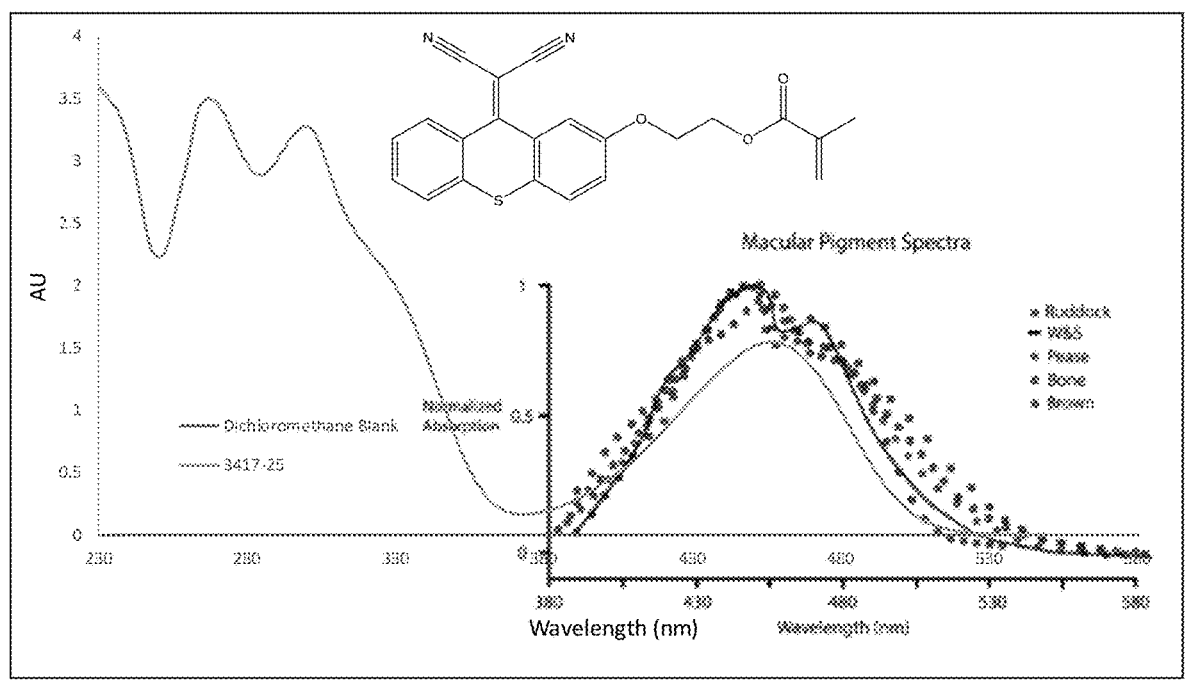
FIG. 2 shows a UV-VIS absorbance spectrum of a 0.2 mM methanolic solution of inventive Compound A superimposed on the literature spectra of macular pigment.

The UV-VIS transmission spectrum of a 0.2 mM methanolic solution of Compound A is shown in FIG. 1. The UV-VIS absorbance spectrum of a 0.2 mM methanolic solution of Compound A superimposed on the literature spectra of macular pigment is shown in FIG. 2.

Example 2

Reactive monomer mixtures are prepared composed of 77 weight percent of the formulations listed in Table 1, and 23 weight percent of the diluent D$_3$O. The reactive monomer mixtures is filtered through a 3 μm filter using a stainless-steel syringe under pressure.

TABLE 1

| Component (weight %) | Ex 2 |
| --- | --- |
| mPDMS | 30-32 |
| SiMAA | 28-30 |
| DMA | 24-25 |
| HEMA | 5.5-6.5 |
| TEGDMA | 1-2 |
| PVP K90 | 6-8 |
| Omnirad 1870 | 0.2-0.4 |
| RB247 | 0.01-0.03 |
| Compound A | 0.05-1 |

The reactive monomer mixture is degassed at ambient temperature by applying vacuum (40 torr) for at least 20 minutes. Then, in a glove box with a nitrogen gas atmosphere and less than about 0.1-0.2 percent oxygen gas, about 75 μL of the reactive mixture is dosed using an Eppendorf pipet at room temperature into the FC made of 90:10 (w/w) Zeonor/TT blend. The BC made of 90:10 (w/w) Z:TT blend is then placed onto the FC. The molds are equilibrated for a minimum of twelve hours in the glove box prior to dosing. Pallets each containing eight mold assemblies are transferred into an adjacent glove box maintained at 65° C., and the lenses are cured from the top and the bottom using 435 nm LED lights having an intensity of about 1.5 mW/cm$^2$ for 3 minutes and then of about 2.5 mW/cm$^2$ for 7 minutes.

The lenses are manually de-molded and released by suspending the lenses in about one liter of 70 percent IPA for about one hour, followed by soaking two more times with fresh 70 percent IPA for 30 minutes; then two times with fresh DIW for 15 minutes; then two time with packing solution for 30 minutes. The lenses are equilibrated and stored in borate buffered packaging solution. A person of ordinary skill recognizes that the exact lens release process can be varied depending on the lens formulation and mold materials, regarding the concentrations of the aqueous isopropanol solutions, the number of washings with each solvent, and the duration of each step. The purpose of the lens release process is to release all of the lenses without defects and transition from diluent swollen networks to the packaging solution swollen hydrogels.

Example 3

A reactive monomer mixture was prepared composed of 77 weight percent of the formulation listed in Table 2, and 23 weight percent of the diluent 3M3P. Compound A was first dissolved in DMA; the resulting solution was then added to another solution containing all of the other components and diluent. The reactive monomer mixture was filtered through a 3 μm filter using a stainless-steel syringe under pressure. The reactive monomer mixture was degassed at ambient temperature by applying vacuum (40 torr) for at least 20 minutes. Then, in a glove box with a nitrogen gas atmosphere and less than about 0.1-0.2 percent oxygen gas, about 75 μL of the reactive mixture was dosed using an Eppendorf pipet at room temperature into the FC made of 90:10 (w/w) Zeonor/TT blend. The BC made of 90:10 (w/w) Z:PP blend was then placed onto the FC. The molds are equilibrated for a minimum of twelve hours in the glove box prior to dosing. Pallets each containing eight mold assemblies were transferred into an adjacent glove box maintained at 65° C., and the lenses were cured from the top and the bottom using 420 nm LED lights having an intensity of about 1.5 mW/cm$^2$ for 3 minutes and then of about 5 mW/cm$^2$ for 5 minutes.

The lenses are manually de-molded and released by suspending the lenses in about one liter of 70 percent IPA for about one hour, followed by soaking two more times with fresh 70 percent IPA for 30 minutes; then two times with fresh DIW for 15 minutes; then two time with packing solution for 30 minutes. The lenses are equilibrated and stored in borate buffered packaging solution. A person of ordinary skill recognizes that the exact lens release process can be varied depending on the lens formulation and mold materials, regarding the concentrations of the aqueous isopropanol solutions, the number of washings with each solvent, and the duration of each step. The purpose of the lens release process is to release all of the lenses without defects and transition from diluent swollen networks to the packaging solution swollen hydrogels. The lenses were stored in vials. After one day of equilibration, the lenses were inspected and sterilized by autoclaving at 122° C. for 30 minutes.

TABLE 2

| Component | Ex 3 (weight %) |
| --- | --- |
| HO-mPDMS (n = 15) | 28 |
| HO-mPDMS (n = 4) | 25 |
| XLMA | 4 |
| DMA | 21 |
| HEMA | 11.33 |
| EGDMA | 0.25 |
| PVP K90 | 9 |
| Omnirad 1870 | 0.25 |
| RB247 | 0.02 |
| Compound A | 0.15 |

Example 4: Light Exposure

Lenses prepared substantially as described in Example 3 were sealed in vials (containing packing solution) by known methods and exposed to light conditions in a glove box. The light conditions used are believed to be at least as harsh as those of ICH guideline Q1B described above (thus equivalent or less photodegradation would be expected under ICH guideline Q1B than observed in this example). The conditions were as follows: 10 vials containing 1 lens each were centered on a glass stage, approximately 4 inches above a 435±5 nm LED panel and exposed to approximately 20 mW/cm$^2$ of radiation for 40 hours at room temperature.

Figure 3:
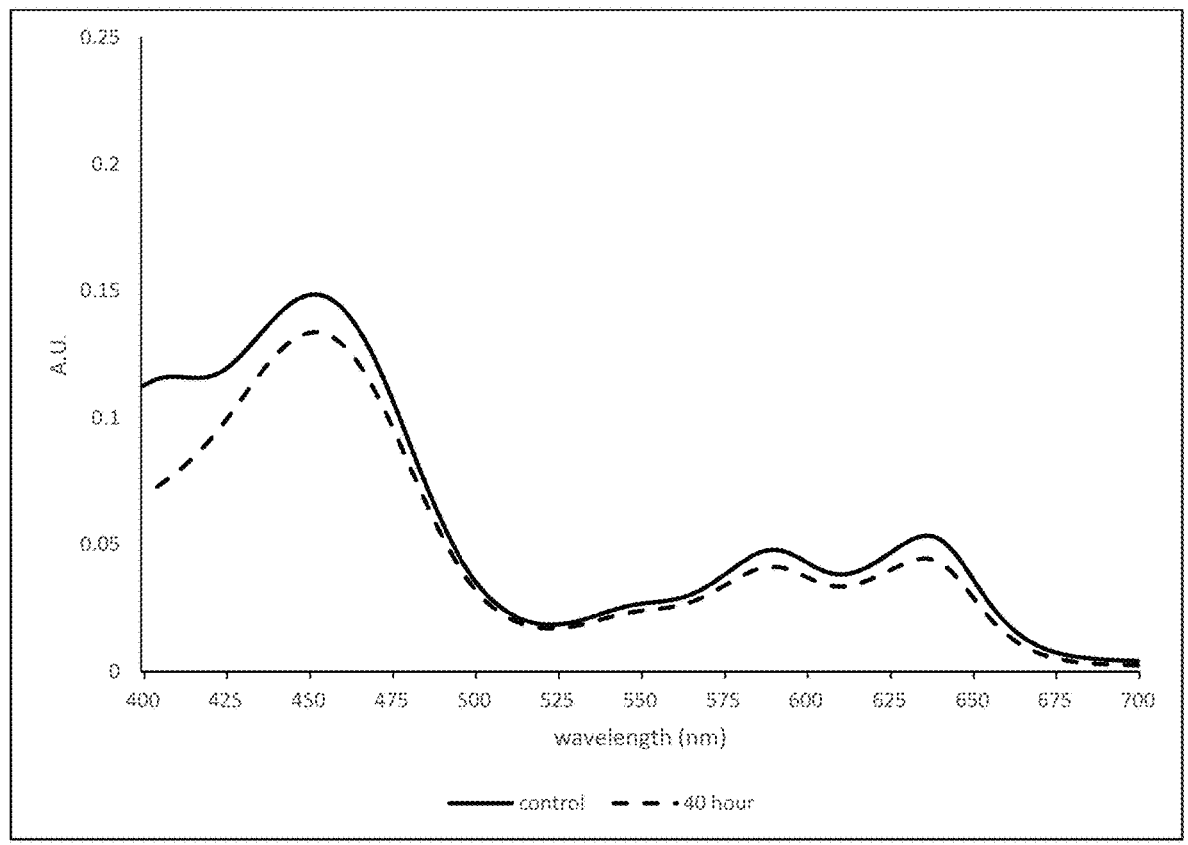
FIG. 3 shows absorbance spectra of contact lenses, prepared from Compound A, following exposure to light for up to 40 hours.

UV/VIS absorbance spectra of the lenses, collected at time zero (control) and at 40 hours are shown in FIG. 3. Absorbance values in the 445 to 455 nm range, as well as the percent change in absorbance following the 40 hour exposure, relative to control, are shown in Table 3. As is apparent from FIG. 3 and Table 3, the tested compound, which shows absorbance around 450 nm that is similar to natural macular pigment, has the added benefit of exhibiting good photostability.

TABLE 3

| Wavelength (nm) | Absorbance (Control) | Absorbance (40 hour) | % change (40 hour) |
| --- | --- | --- | --- |
| 455 | 0.14782 | 0.13311 | 9.9 |
| 454 | 0.14820 | 0.13344 | 10.0 |
| 453 | 0.14845 | 0.13365 | 10.0 |
| 452 | 0.14853 | 0.13369 | 10.0 |
| 451 | 0.14846 | 0.13358 | 10.0 |
| 450 | 0.14830 | 0.13338 | 10.1 |
| 449 | 0.14796 | 0.13303 | 10.1 |
| 448 | 0.14749 | 0.13258 | 10.1 |
| 447 | 0.14681 | 0.13190 | 10.2 |
| 446 | 0.14610 | 0.13119 | 10.2 |
| 445 | 0.14526 | 0.13034 | 10.3 |

I claim:

1. A compound comprising a chromophore, the chromophore having a substructure of formula I:

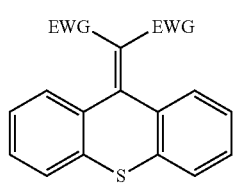

(I)

wherein EWG at each occurrence is independently an electron withdrawing group, the compound having a visible light absorption maximum between 430 and 480 nm and a full width half maximum (FWHM) at the visible light absorption maximum of at least 35 nm and up to 100 nanometers, wherein the compound is photostable.

2. The compound of claim 1 wherein EWG at each occurrence is independently cyano, amide, ester, keto, or aldehyde.

3. The compound of claim 1 wherein EWG at each occurrence is cyano.

4. The compound of claim 1 that is of formula II:

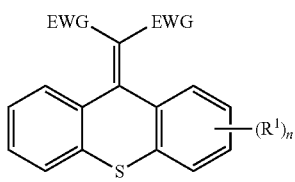

(II)

wherein EWG at each occurrence is independently an electron withdrawing group; n is 1, 2, or 3; and $R^1$ is at each occurrence is independently H, $C_1$-$C_6$ alkyl, $C_1$-$C_6$ alkoxy, $C_1$-$C_6$ thioalkyl, $C_3$-$C_7$ cycloalkyl, aryl, halo, hydroxy, amino, $NR^3R^4$, benzyl, $SO_3H$, or $SO_3M$ (M is a monovalent cation, such as sodium or potassium), or —Y—$P_g$, wherein $R^3$ and $R^4$ are independently H or $C_1$-$C_6$ alkyl, Y is a linking group; and $P_g$ is a polymerizable group.

5. A compound according to claim 1 that is:
2-((9-(dicyanomethylene)-9H-thioxanthen-2-yl)oxy) ethyl methacrylate.

6. The compound of claim 1 wherein the visible light absorbance maximum is between 440 nm and 470 nm.

7. The compound of claim 1 wherein the FWHM at the visible light absorption maximum is at least 40 nm and up to 95 nm.

8. The compound of claim 1 wherein photostability comprises a loss of absorbance at the visible light absorption maximum of no more than 20 percent.

9. The compound of claim 1, wherein the compound is more photostable than macular pigment.

10. An ophthalmic device comprising a compound according to claim 1.

11. A contact lens or intraocular lens that is a polymerization reaction product of a reactive mixture comprising: a monomer suitable for making the ophthalmic device; and (b) a compound according to claim 1.

12. A spectacle or sunglass lens comprising (a) a mineral material or an organic material or combination thereof, and (b) a compound according to claim 1.

13. An optical device comprising a compound according to claim 4 that is: 2-(9H-thioxanthen-9-ylidene)malononitrile; or
2-((9-(dicyanomethylene)-9H-thioxanthen-2-yl)oxy) ethyl methacrylate.

* * * * *